(12) United States Patent
Cheng et al.

(10) Patent No.: US 6,289,895 B1
(45) Date of Patent: Sep. 18, 2001

(54) URETHRAL COMPRESSION DEVICE

(75) Inventors: Gordon Cheng, Carlisle; Sanjaya Kumar, Southborough; Richard Beane, Hingham; Richard Simmers, Gloucester, all of MA (US)

(73) Assignee: UroScientific, Inc., Woburn, MA (US)

( * ) Notice: Subject to any disclaimer, the term of this patent is extended or adjusted under 35 U.S.C. 154(b) by 0 days.

(21) Appl. No.: 09/301,184

(22) Filed: Apr. 28, 1999

Related U.S. Application Data

(63) Continuation-in-part of application No. 09/067,522, filed on Apr. 28, 1998, now Pat. No. 6,234,174.

(51) Int. Cl.[7] .................................................. A61F 5/48
(52) U.S. Cl. ................................. 128/885; 128/DIG. 25; 600/29
(58) Field of Search .................................. 128/846, 885, 128/886, DIG. 25; 600/29–31

(56) References Cited

U.S. PATENT DOCUMENTS

| | | | |
|---|---|---|---|
| 3,147,754 | 9/1964 | Koessler | 128/346 |
| 3,866,611 | 2/1975 | Baumrucker | 128/346 |
| 4,139,007 | 2/1979 | Diamond | 128/138 R |
| 4,534,353 | 8/1985 | de Leur et al. | 128/346 |
| 4,800,900 | 1/1989 | French | 128/885 |
| 4,880,016 | 11/1989 | Worth et al. | 128/885 |
| 4,942,886 | 7/1990 | Timmons | 128/885 |
| 5,184,629 | 2/1993 | Erickson et al. | 128/885 |
| 5,211,640 | 5/1993 | Wendler | 604/349 |
| 5,263,947 | 11/1993 | Kay | 604/331 |
| 5,415,179 | 5/1995 | Mendoza | 128/842 |
| 5,439,007 | 8/1995 | Fischer | 128/842 |
| 5,569,297 | 10/1996 | Makower et al. | 606/201 |
| 5,571,125 | 11/1996 | Chadwick | 606/157 |

*Primary Examiner*—Michael A. Brown
(74) *Attorney, Agent, or Firm*—Hamilton, Brook, Smith & Reynolds, P.C.

(57) ABSTRACT

A urethral compression device prevents male urinary incontinence by compressing the urethra. The device has a longitudinally extending pressure-applying element. The urethral compression device compress the urethra without applying undue force to other parts of the penis. The device incorporates a latching mechanism for the purpose of securing the device in a locked position with the pressure-applying element compressing the urethra of the penis. The device is designed to allow the user to manipulate the device using only one hand, if so desired.

39 Claims, 18 Drawing Sheets

URETHRAL COMPRESSION DEVICE

RELATED APPLICATIONS

This application is a Continuation-In-Part of U.S. application Ser. No. 09/067,522, filed on Apr. 28, 1998, now U.S. Pat. No. 6,234,174 the entire teachings of which are incorporated herein by reference.

BACKGROUND OF THE INVENTION

Male urinary incontinence can result from a variety of physical or neurological conditions. The incidence of incontinence increases with advanced age. Surgical treatment of prostate cancer or benign prostatic hyperplasia (BPH), such as radical prostatectomies, open or transurethral prostatectomy, and trauma to the membranous urethra or bladder neck can all cause temporary or permanent incontinence in men.

Existing external compressive incontinence control devices are based on the principle that if the entire cross-section of the penile shaft is sufficiently compressed, the urethra will be correspondingly flattened to prevent any urine leakage. In order to prevent the urine leakage, the penis must be flattened to about 40% or more of the normal penile diameter. When a conventional penile clamp is used with this level of compression, the major side effect is constriction of blood vessels and prevention of blood circulation to the penis. While most users of the penile clamps of these types learn to periodically remove the clamps to temporarily restore blood circulation, it is nonetheless a major inconvenience. In addition, these conventional devises are heavy and bulky, uncomfortable and insufficiently discreet.

Others have recognized that it would be desirable to selectively compress the urethra, which is situated along the central underside of the penile shaft, without exerting undue compression of the entire penile shaft. While these devices compress the urethra more than the body of penis, the devices are either too bulky, which detracts from the user's comfort level and privacy, or are comprised of many components which increase the complexity and cost of the device and the probability of failure. Also, many of the devices require two hands for application or removal.

SUMMARY OF THE INVENTION

This invention relates to a urethral compression device. The urethral compression device has a compression element which extends longitudinally, so that when engaging the penis the compression element extends parallel to the urethra to compress the urethra. A latching mechanism retains the urethral compression device in the position to compress the urethra In a preferred embodiment, the urethral compression device has an arced shaped element having a first and a second arm A compression element that applies pressure is carried by the arced element for compressing the urethra. The compression device can be made of a molded plastic material that is positioned in an open state when in an unstressed condition. The user bends one arm to connect the ends of the arms together and places the device under stress in the closed position. In a preferred embodiment, the user can easily remove the device when the arc shaped element is in the open unstressed state.

In a preferred embodiment of the invention, the pressure applying or compression device has a width of between 100 percent and 150 percent of the diameter of the urethra for optimally compressing the urethra and minimally compressing the rest of the penis. The device can be fabricated in a number of different sizes as needed.

In a preferred embodiment, the device has a latching mechanism including a plurality of teeth carried by one arm and a pawl on the other arm to engage the teeth for retaining the arced shaped element in a closed position. The arced shaped element is biased towards an open position such that release of the arms opens the device.

The urethral compression device provides a male urinary incontinence control device that is effective, non-invasive, reliable, comfortable and easily adjustable without complicated construction, adjustment procedures, or accessories. In addition, the design of the device also ensures that the user is able to maintain a high degree of privacy without being noticed by others when the user is wearing and manipulating the device.

By applying pressure selectively to the area of urethra, the urethra can be sufficiently compressed or occluded to prevent urine flow without exerting undue pressure to other parts of the penis or reducing blood circulation.

In a preferred embodiment, the urethral compression device is structured without an apparent localized hinge point. Because of the properties inherent in the construction materials, the device is provided with sufficient flexibility to allow the opening and closing of the pair of ends.

In several embodiments, the urethral compression device has a pair of distinct latching mechanisms to retain the device around the penis and to compress the urethra. The compression of the urethra in those embodiments is accomplished by a compression hinge which closes and forms a pressuring device as the compression hinge is moved towards the urethra. The second or compression latching mechanism holds the compression hinge in position.

In a preferred embodiment, the urethral compression device has a strap, a closure latching mechanism, a compression latching mechanism, and a compression hinge. The device has a pair of substantially flat pressure-applying elements hinged together at the compression hinge. The compression latching mechanism which works in conjunction with the compression hinge to compress the urethra. The latching mechanism, in a preferred embodiment, has a plurality of teeth which define receptacles and an engaging tab.

The second ends of the flat pressure-applying elements are moved towards each other, therein moving the compression hinge perpendicular towards the penis to compress the urethra. The moving of the second ends of the flat pressure-applying elements results in moving of the compression latching mechanism into a closed latched position retaining the compression hinge against the penis.

The closure latching mechanism, in a preferred embodiment, has a locking tab which projects inwardly into a receptacle which receives the strap. To secure the urethral compression device around the user's penis, the strap is threaded through the receptacle and secured by engaging the locking tab against the strap.

The urethral compression device can be opened for urination, closed after urination, and adjusted to the desired degree of compression by the user using only one hand, without the need for necessarily using the other hand.

The urethral compression device does not need to be removed from the penis in order to allow the user to urinate. When the device is in place and is opened for urination, the ends of the device springs open such that the opened device remains on the penis shaft. This functionality is provided to avoid the necessity of removing the device from the penis shaft, when it is supported by the user during urination.

The size, weight and operational simplicity afford a particular discreteness to this invention. The design of the invention allows the wearer to use the urethral compression device without detection since the invention does not inhibit normal body movements. The small size of the invention does not add obvious volume bulk beneath user's clothing.

DESCRIPTION OF TEE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Figure 22:
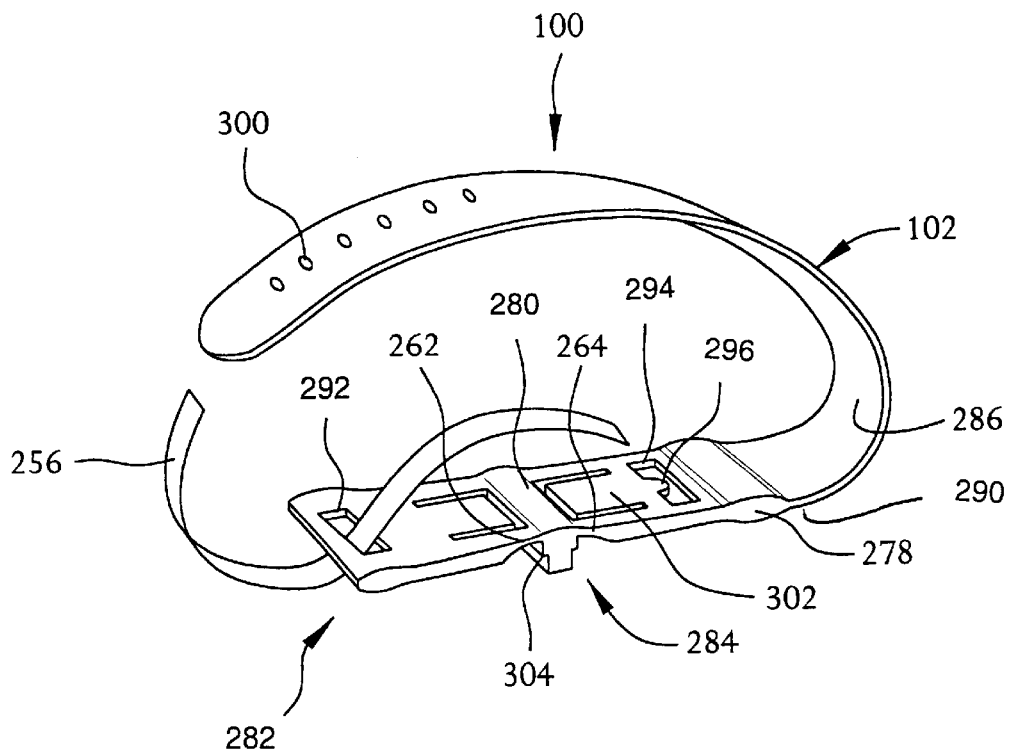
FIG. 22 shows an alternate embodiment of a urethral compression device.
Figure 23:
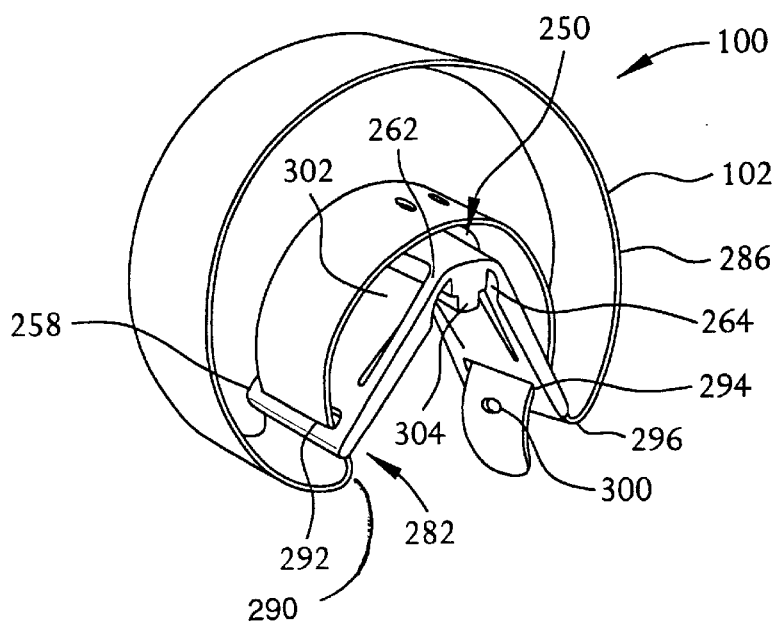
Figure 24:
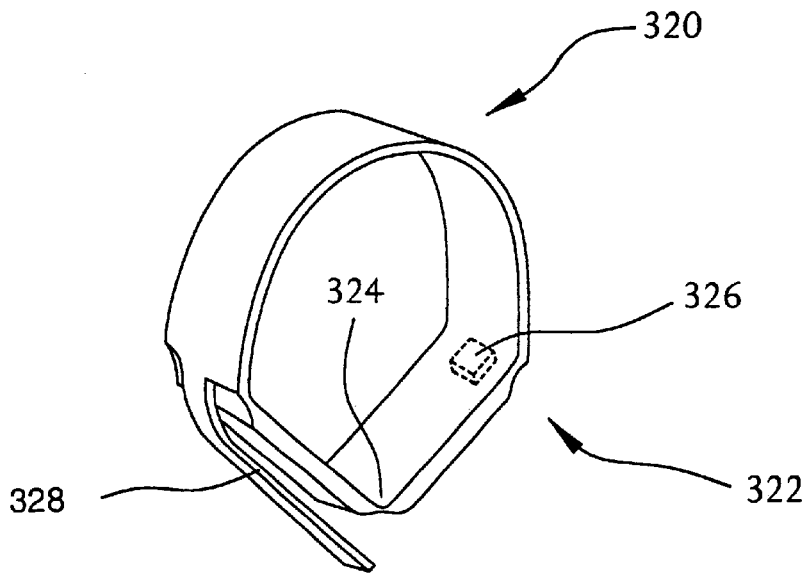
Figure 25:
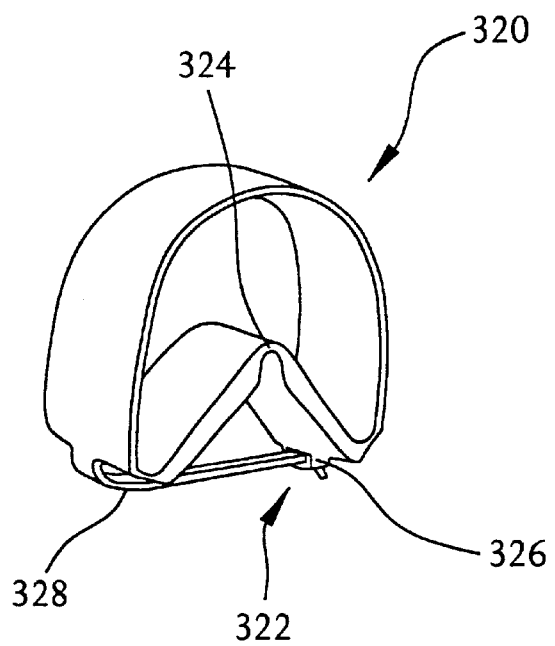
Figure 26:
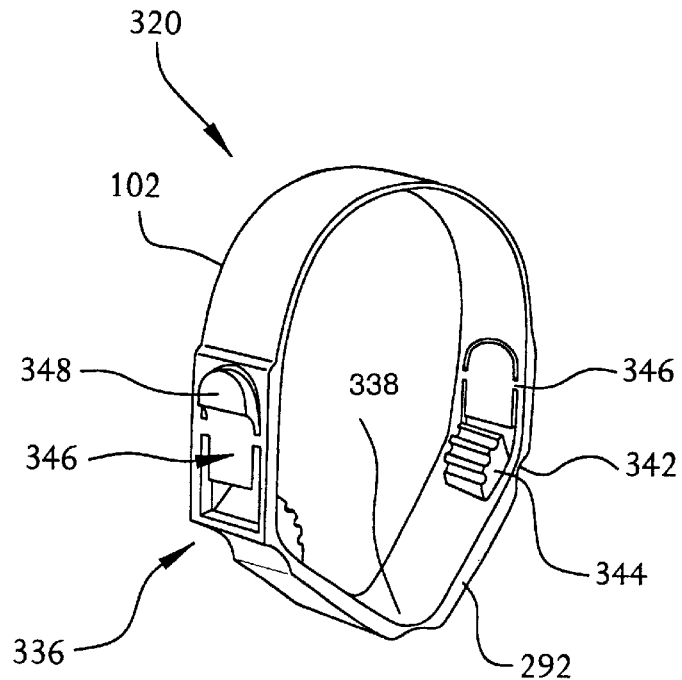
Figure 27:
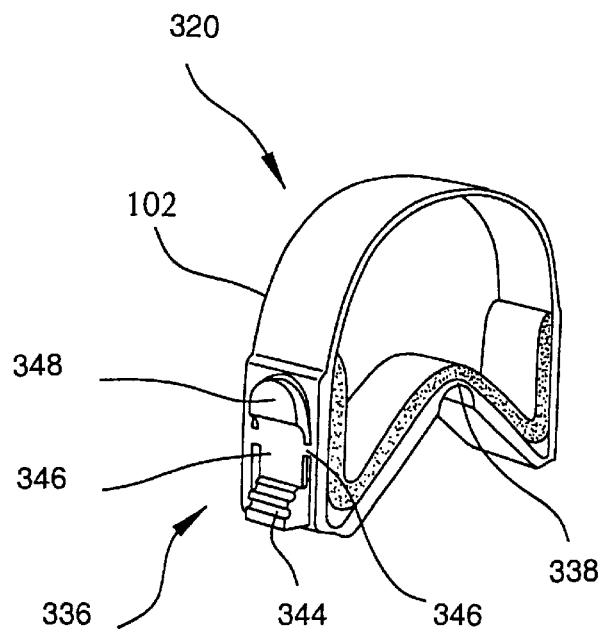
Figure 28:
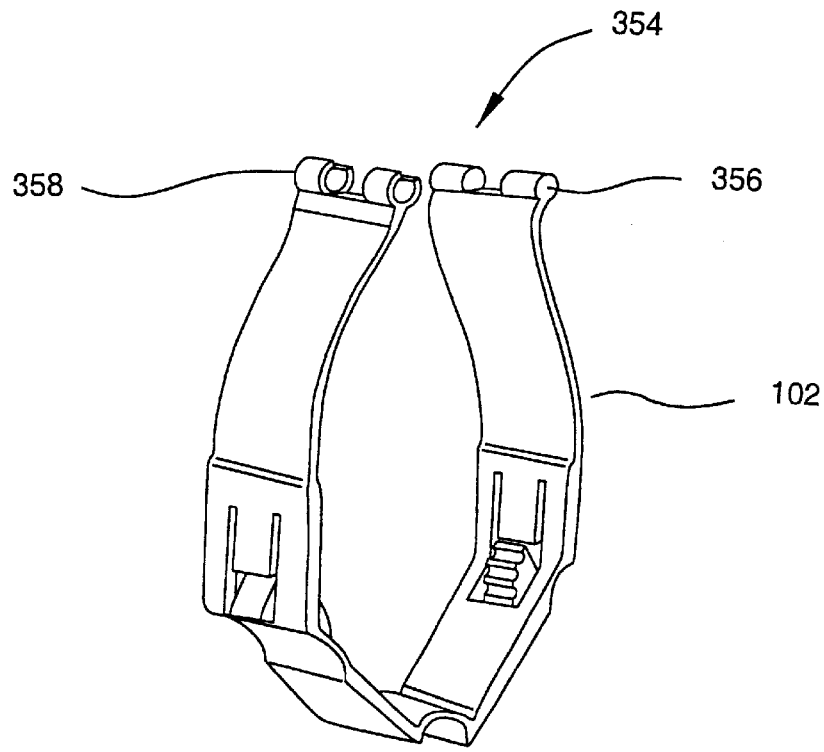
Figure 29:
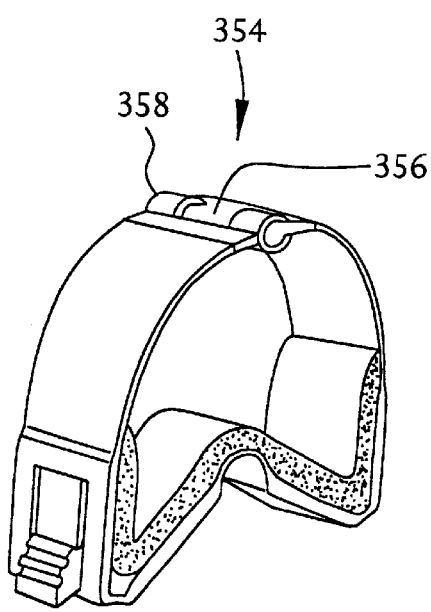
Figure 30:
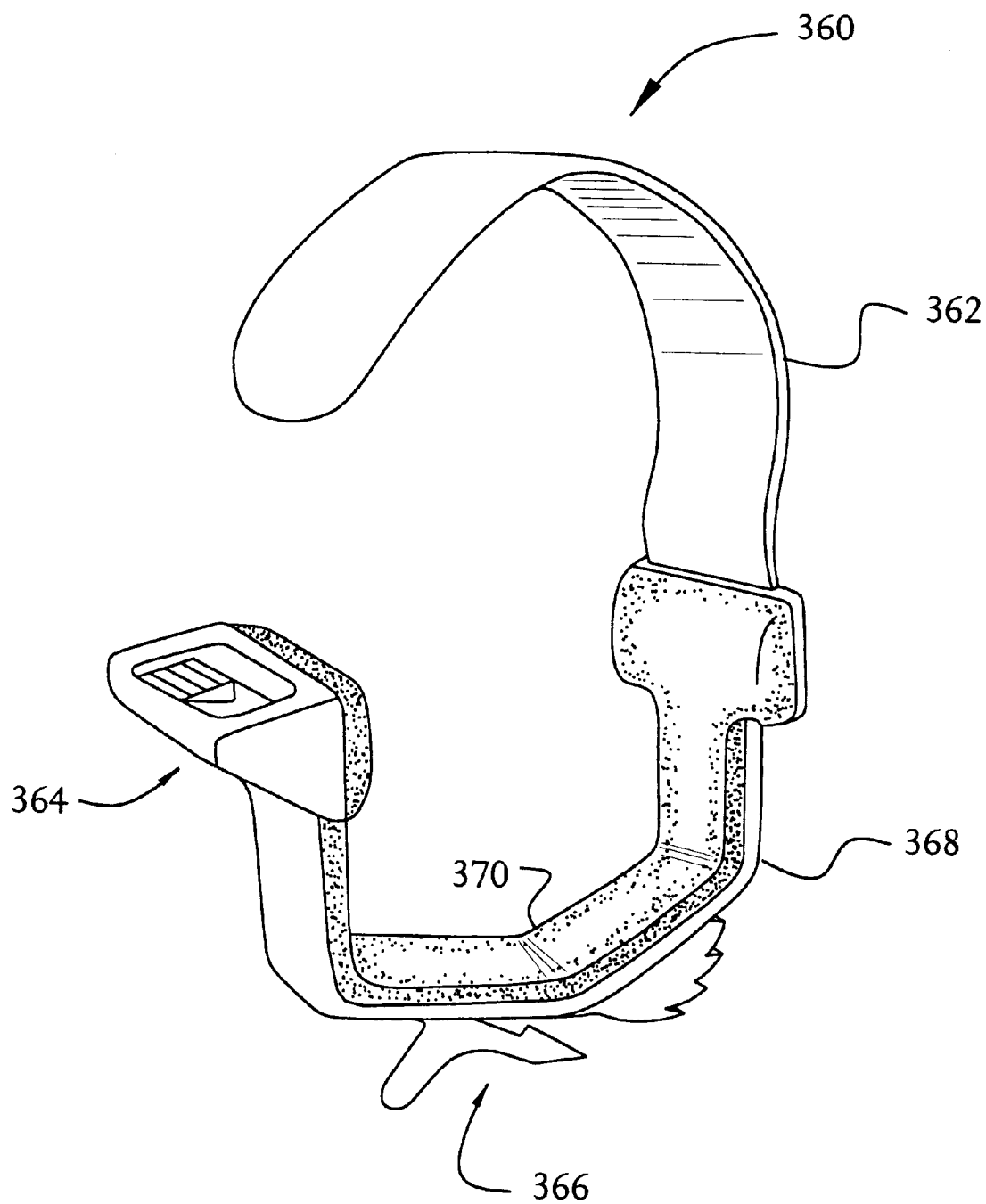
Figure 31:
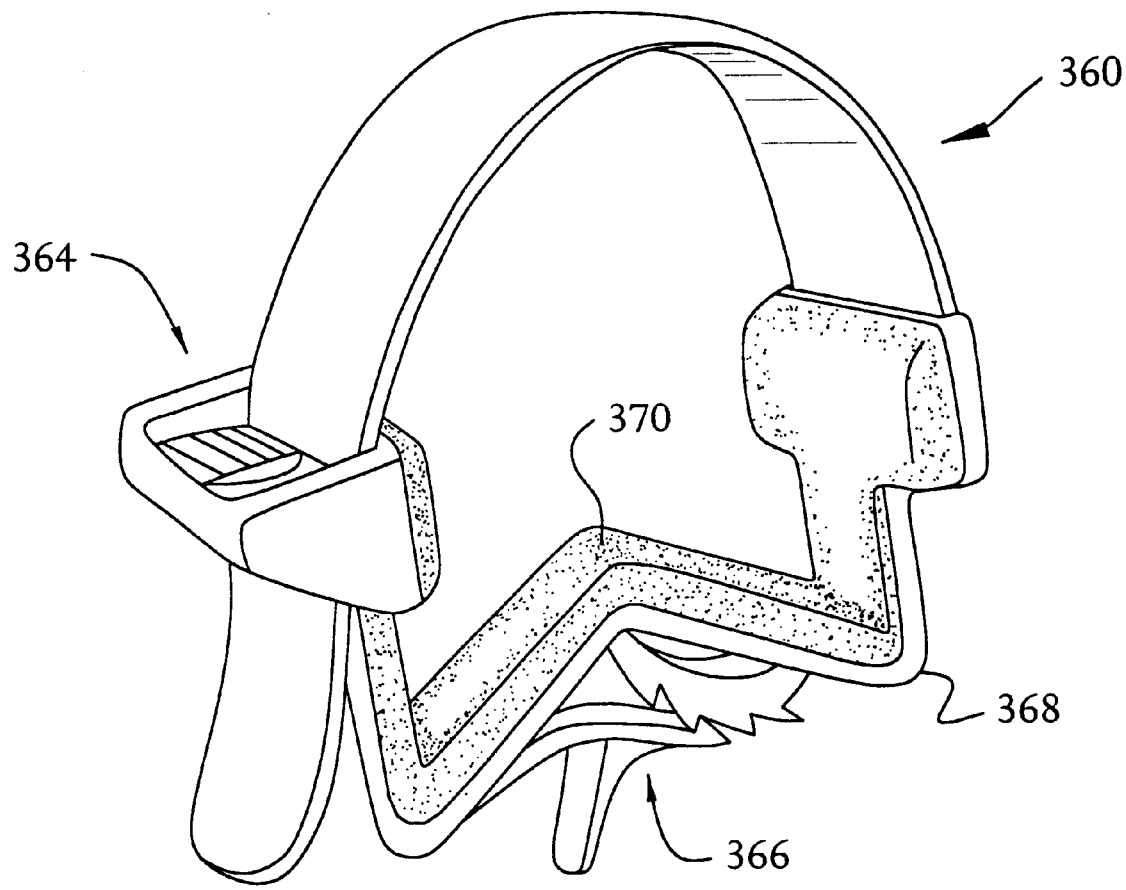

FIG. 23 the urethral compression device in FIG. 22 with the first and second latching mechanisms in an engaged state;

FIG. 24 illustrates another embodiment of a urethral compression device, one latching mechanism in an unengaged state;

FIG. 25 illustrates the urethral compression device of FIG. 24 having one latching mechanism in an engaged state;

FIG. 26 illustrates an alternate embodiment of a urethral compression device having one latching mechanism;

FIG. 27 illustrates the urethral compression device of FIG. 26 with the latching mechanism in an engaged state;

FIG. 28 shows an alternate embodiment of the invention illustrated in FIG. 26;

FIG. 29 shows the urethral compression of FIG. 28 with the latching mechanism in a position similar to that shown in FIG. 27;

FIG. 30 illustrates a perspective view of an alternative embodiment of a urethral compression device with a first and a second latching mechanism in an unengaged state; and FIG. 31 illustrates the urethral compression device of FIG. 30 with both the first and the second latching mechanisms in an engaged state.

DESCRIPTION OF THE INVENTION

Referring to the drawings in detail, where like numerals indicate like elements, there is illustrated an urethral compression device in accordance with the present invention designated generally as 10.

The urethral compression device 10 is generally an arced shaped structure 12 having an upper arm 14 and a lower arm 16. In this embodiment, the arced structure 12 has generally a "C" shaped structure. Each of the arms 14 and 16 terminate in a first end 18 and a second end 20 where the ends extend around an arc of at least 270 degrees. The arms 14 and 16 are adapted to couple as explained below to form a generally cylindrical compression device 10.

Figure 1:
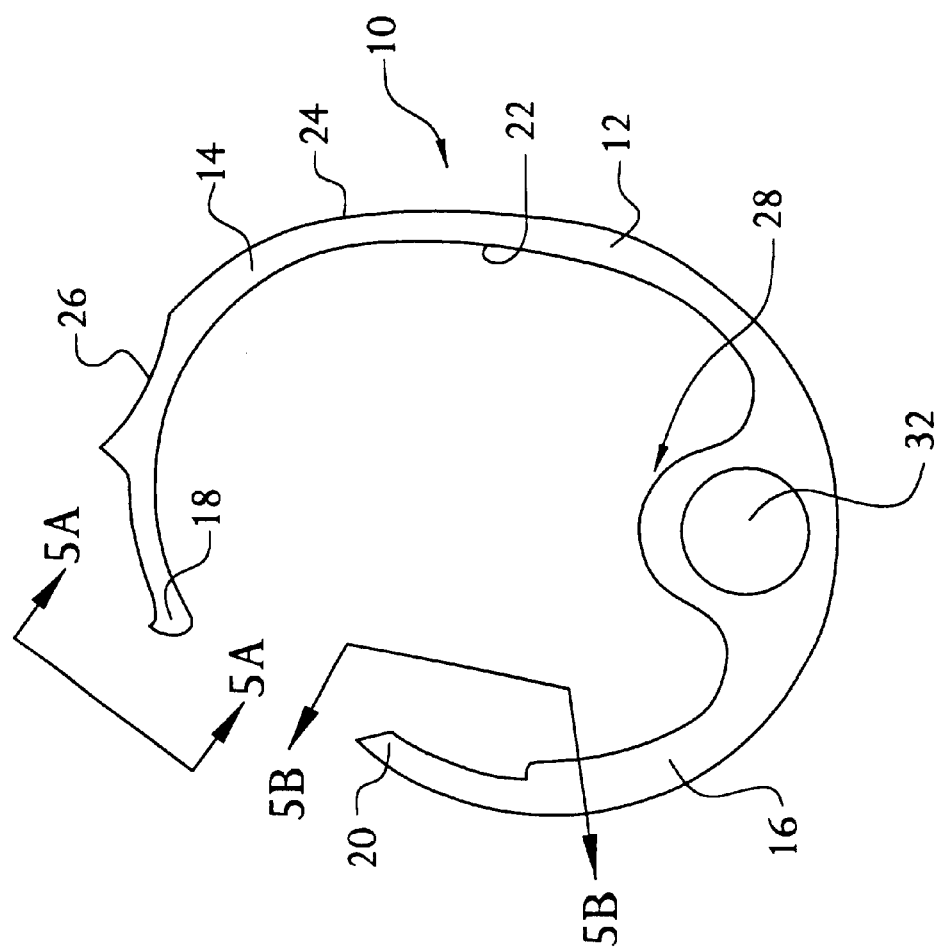
FIG. 1 is a front view of a urethral compression device according to this invention in an open position.

In a preferred embodiment, the structure 12 is manufactured as one continuous piece of material. The material is formed such that the structure 12 is biased to an open position shown in FIG. 1, wherein the first end 18 and the second end 20 are spaced from each other, and not engaged. The structure 12 in the open position receives the penis without compressing the penis as described below.

The device 10 has an inner surface 22 and an outer surface 24. The device 10 can have a thumb tab 26 on the outer surface 24 of the upper arm 14. The device 10 has a pressure-applying element 28 projecting inwardly on the inner surface of the lower arm The pressure-applying element 28 has a raised portion which is sufficiently wide to optimally compress the urethra to prevent urine leakage while minimally compressing the bulk of the penis.

In a preferred embodiment, the pressure-applying element 28 extends radially inward and is formed integrally as one piece with the arced shaped structure 12. The radially extending element 28 may be formed with a hole 32, or a cavity, with various shapes or geometries for minimizing the weight of the device 10. The presence or absence of a hole does not change the mode of operation.

In a preferred embodiment, the urethral compression device 10 is molded or extruded and made of a polymer material. The thickness of the arms 14 and 18 of the arced shaped structure 12 is generally in a range of 11 mm to 5 mm, and between 1 mm to 2 mm in a preferred embodiment. The device can be fabricated with a variety of polymer materials such as polyethylene, polypropylene, nylon, or polycarbonate, either in pure form, plasticized form, or composited with other polymers or filler materials. The filler material can include carbon fiber, glass fiber or other suitable filler. The device can also be constructed with an inner core of one material, such as a metal, and outer surface of some other material such as a polymer by coating, lamination or other adhesion techniques.

In a preferred embodiment, the element 28 is cylindrically shaped and has a diameter in the range of 10–15 mm. In order to achieve the desired benefits of this invention, both the size of the arced structure 12 and the element 28 are tailor to fit to the individual users. This is accomplished by presenting the urethral compression devices in a series of sizes in which arced shaped structure 12 will vary by the size of the penis and the element 28 will vary in accordance with the size of the urethra, as explained below.

Figure 2:
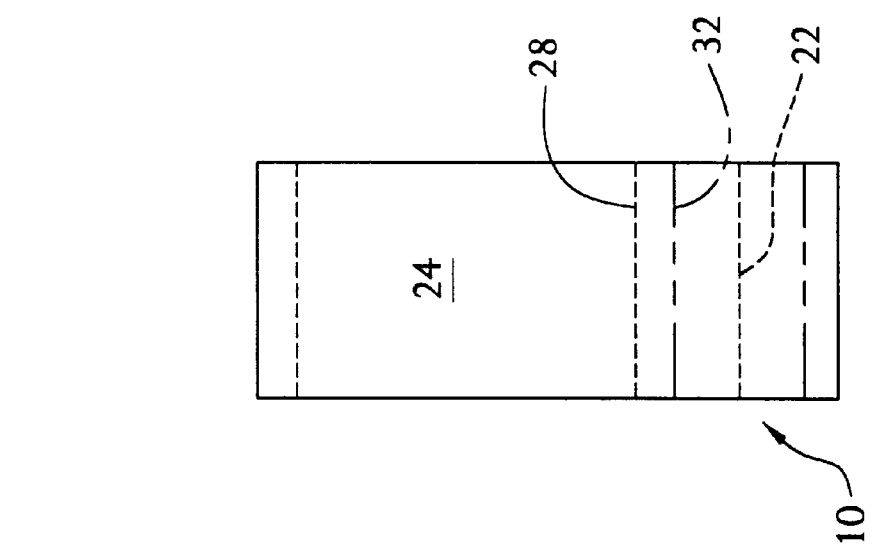
FIG. 2 is a side view of the urethral compression device.

A side view of the urethral compression device 10 is shown in FIG. 2. The device 10 is generally uniform in its width. The inner surface of the upper arm 22 is shown in hidden line. The inner surface of the lower arm including the pressure-applying element 28 is shown in hidden line. The hole 32 extending through the element 28 is shown in phantom In a preferred embodiment, the urethral compression device 10 has a width in the range of 10 mm to 25 mm and in the most common size having an approximate width of 15 mm.

Figure 3:
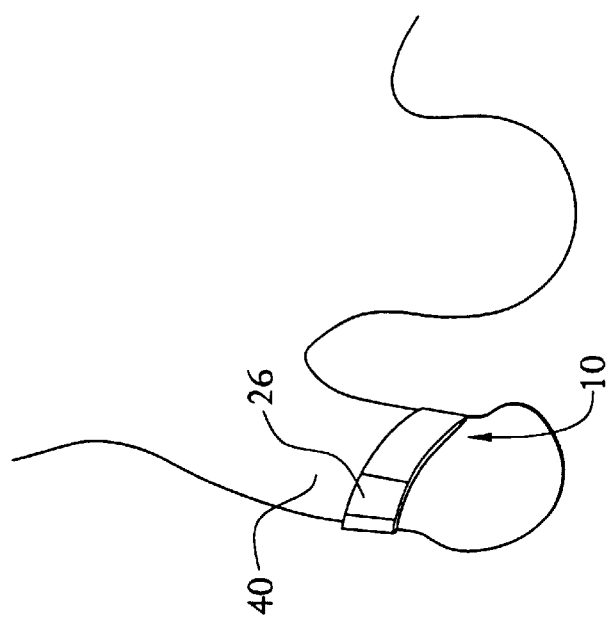
FIG. 3 is a perspective view of the urethral compression device in a closed position encircling the penis.

FIG. 3 illustrates the urethral compression device 10 on a penile shaft 40. The user typically slides the urethral compression device 10 over the penis 40, however, the arms 14 and 16 can be sufficiently separate such that the penis can pass between the upper end 18 and the lower end 20 shown in FIG. 1.

Figure 4:
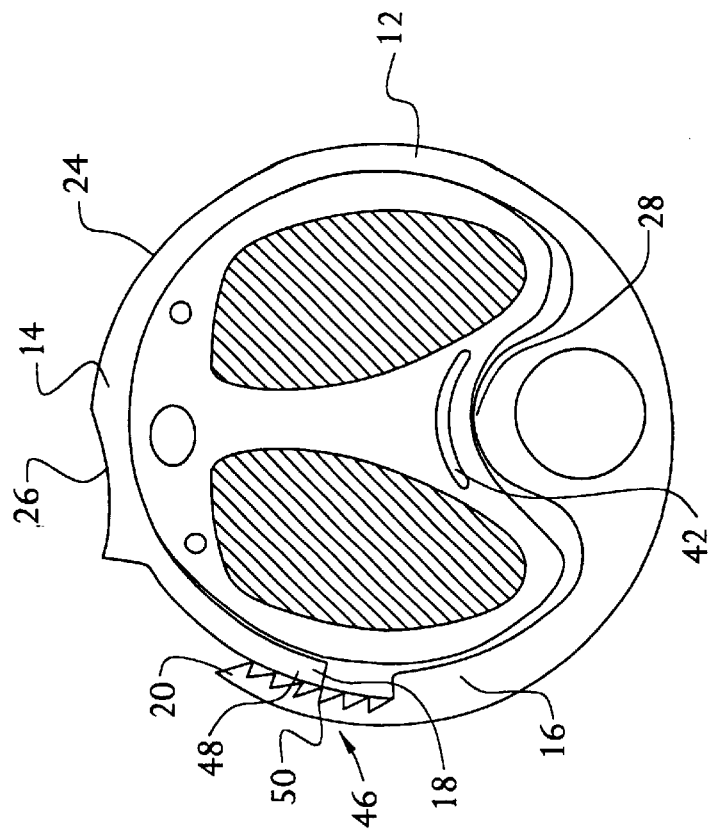
FIG. 4 is a cross sectional view of the urethral compression device in a closed position encircling the penis.

With the urethral compression device 10, in an open position, encircling the penis 40, the user positions the device 10 such that the pressure-applying element 28 is located under the urethra 42, as seen in FIG. 4. The user presses the thumb tab 26, while holding the lower arm 16 of the urethral compression device 10 with other fingers.

Figure 5B:
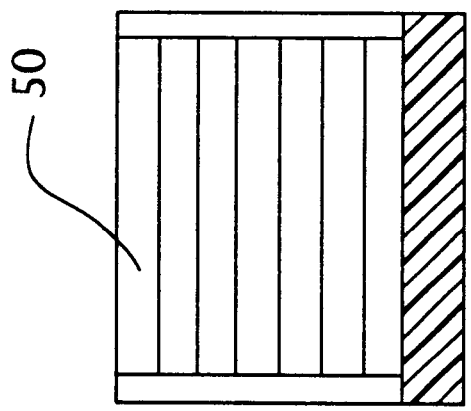
FIG. 5B is a sectional view of the ratchet teeth taken along line 5B—5B in FIG. 1.
Figure 5A:
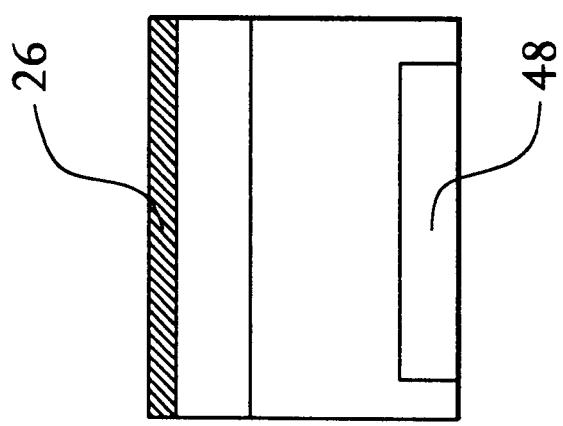
FIG. 5A is a sectional view of the pawl taken along line 5A—5A in FIG. 1.

Still referring to FIG. 4, the arms 14 and 16 of the arced structure 12 have a latching mechanism 46 near the ends 18 and 20 to hold the urethral compression device 10 in a closed position, as shown. In a preferred embodiment, the latching mechanism 46 has a pawl 48 on one arm and a plurality of ratchet teeth 50 on the other arm One of the arms, the upper arm 14 as shown in FIG. 4, has the pawl 48 projecting outward. The pawl 48 extends across over half of the width of the device 10 as seen in FIG. 5A.

The other arm, the lower arm 16 as shown in FIG. 4, has the plurality of ratchet teeth 50 projecting inward. The teeth 50, similar to the pawl 48, extend across over half the width of the device as seen in FIG. 5B.

In the preferred embodiment, the ratchet teeth 50 are formed on the lower arm 16 and the pawl 48 is formed on the upper arm 14. It is recognized that the arrangement can be reversed with the pawl on the lower arm and the ratchet teeth on the upper arm. It is further recognized that the arrangement in which the ratchet teeth are made to project outward with a corresponding inward projecting pawl is also within the context of this invention.

Referring back to FIG. 4, the ends 18 and 20 of the arms 14 and 16 are ramped so that upon sliding the arms together, the pawl 48 moves into engagement with one of the ratchet teeth 50. The interlocking of the two ends 18 and 20 is designed to provide audible "clicks" when the pawl 48 snaps into each locking position with the teeth 50. The sound serves to notify the user how many ratchet teeth 50 the pawl 48 has passed or engaged so that user can determine when the precise engagement position of the device is reached. In the preferred embodiment of the invention, the user must exert 1.5–3.0 pounds force on the arms 14 and 16 to cause the two ends 18 and 20 to initially engage.

The thumb tab 26, in addition to being used to direct the proper force for engaging the pawl 48 with the ratchet teeth 50, can also be used for unclasping device. Once in place, the user can unclasp the device either by depressing the thumb tab 26 toward penis 40 or by prying away the inclined tip of the lower arm 16 by approximately 1 mm with a tip of a finger to disengage the pawl 48 from the ratchet teeth 50, while holding the base of the device in the palm of the hand. Either of these procedures can be performed using only one hand. The inherent elasticity of the material and the design of the structure itself permits the device to spring to the open position when the pawl 48 is disengaged from the ratchet teeth 50.

In alternate embodiments, other methods can be used to cause the device to spring to the open position. One such method includes varying the width of the urethral compression device 10 along its circumference in specific areas. Decreasing the width of the urethral compression device 10 will increase the flexibility of the material in that area.

Another method includes varying the thickness of the urethral compression device 10 in certain areas. Decreasing the thickness of the urethral compression device 10 in one area will increase the flexibility of the compression device 10 in that area.

Another method to tailor the amount of force needed to open and close the urethral compression device 10 is by choosing a material with a specific modulus of elasticity. The modulus of elasticity of the urethral compression device 10 will control the extent to which the device springs to an open position when unclasped. A device 10 comprised of a material with a high modulus of elasticity will spring open faster than a device 10 comprised of a material with a lower modulus.

Adding bracing or ribbing to certain areas of the outer circumference of the device 10 also controls the flexibility of the device 10, allowing the device 10 to spring to an open position in certain cases. The addition of bracing or ribbing would decrease the flexibility of the device 10 in general. An area of the urethral compression device 10 with no bracing has a greater degree of flexibility than an area with bracing. It is recognized that any or all of these tailoring methods can be used alone or in combination with each other to produce the desired flexibility of the device 10.

The pressure applying device 28 of the urethral compression device 10 has a width that compresses the user's urethra 42 while preventing the user from feeling pinched by unnecessary compression of the penile shaft 40. When the device is in the open position and has been correctly fitted for the user's anatomy, it will accommodate the penis in an uncompressed state. When the device is in a closed position, the pressure-applying element 28 provides a pre-determined degree of depression necessary for preventing involuntary urinary flow.

The ratchet teeth 50 and the pawl 48 of the latching mechanism 46 allow for the graduated adjustments in the degree of compression of the user's urethra 42.

To further understand how the urethral compression device 10 works, a brief description of the male urinary tract is needed. The inner diameter of the urethra, which varies among individuals, could range from 18 to 30 French (or 6 millimeter to 9.5 millimeter) (3 French=1 mm). The wall thickness of urethra varies between 1 to 1.5 mm. The outer diameter of the urethra varies from 7 to 11.5 mm.

In order to completely prevent the leakage of the urine with a penile clamping device, the vertical dimension of the urethra needs to be compressed into no more than the two wall thickness of the urethra. For example, let us use some typical measurements:

Penile outer diameter –31.8 mm
Urethra inner diameter –8.3 mm
Urethra outer diameter –10.7 mm
Urethra wall thickness –1.2 mm With the above typical measurements, the urethra vertical dimension (or the urethra outer diameter) must be flattened by compression from 10.7 mm to no more than 2.4 mm (two urethra wall-thickness). This represents a "degree of compression," defined as reduction in the outer urethra vertical dimension in the compressed state from the uncompressed urethra outer diameter (10.73–[2×1.2]=8.33) divided by the uncompressed urethra outer diameter, (10.7), expressed in percentage, of 78%. (0% represents no compression and 100% represent total compression.)

The urethral compression device 10 has the pressure-applying element 28 at the base of the device 10 to flatten the urethra. The size of this element 28 is approximated by the outer diameter of the urethra. If the penile OD=31.8 mm (same as the in the above illustration) and the element 28 OD is assumed to be 13.914 mm (30% larger in diameter than the urethra OD of 10.7 mm), the overall resultant degree of compression for this device can be computed to be 19% by taking the ratio of the cross-sectional area of the penis compressed by the element 28, or simply the pressure-applying element area, and the cross-sectional area of the un-compressed penis. A higher degree of compression corresponds to a stronger feeling of being pinched. For comparison, to effect the same degree of urethra flattening, the conventional penile clamping devices require a degree of depression of 78%.

In a preferred embodiment, the urethral compression device 10 is sized for the user such that the inner diameter of the circle formed by the closed device with the pressure-applying element 28 removed is the same diameter as the outer diameter of the penis. The urethral compression device 10 in the open position receives the penis without the pressure-applying element 28 compressing the urethra. The pressure-applying element 28 has a size in the range of 100% to 150% of the outer diameter of the urethra In a preferred embodiment, the element 28 is in a range of 110% to 140% of the diameter of the urethra.

Figure 6:
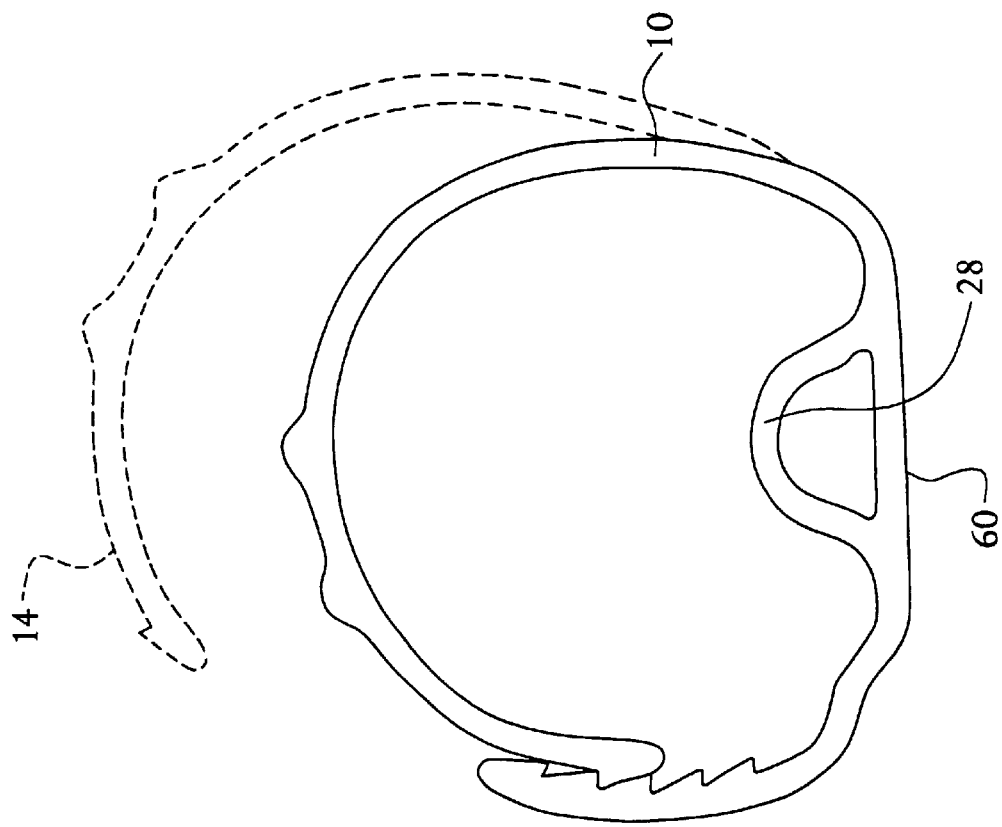
FIG. 6 is a front view of an alternate embodiment of a urethral compression device in a closed position. The upper arm in an open position is shown in phantom.

FIG. 6 shows a preferred embodiment of the invention in a closed position. The invention has a flat surface 60 which is located distal to the pressure-applying element 28. The flat surface 60 provides the user some frame of reference when applying the invention to a penis wherein the flat surface 60 can be used by the user to locate the urethra. When installed properly, the flat surface 60 will be the lower surface. This will cause the element 28 to align with the wearer's urethra, thus allowing proper installation of the device.

The upper arm 14 is shown in phantom in FIG. 6. The penis fits in an uncompressed state into the urethral compression device 10 when the urethral compression device 10 is in the open position.

Figure 7:
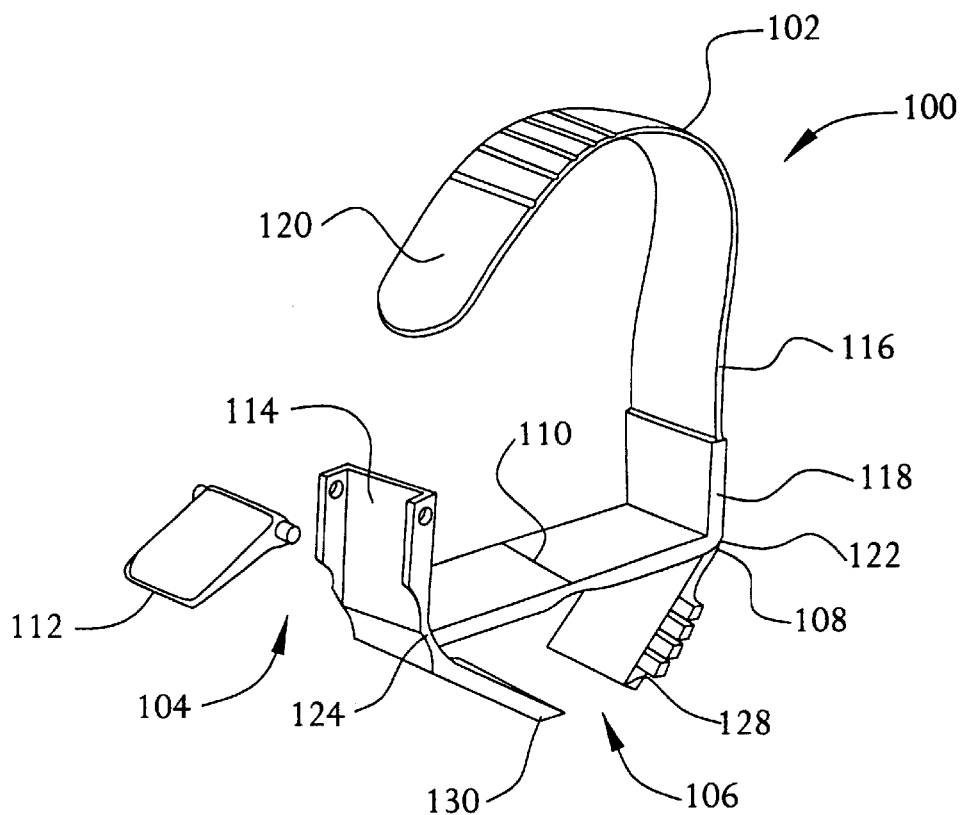
FIG. 7 illustrates a perspective view of an alternative embodiment of the urethral compression device having a cam of a first latching mechanism exploded away. A second latching mechanism for compressing the urethra is shown in an open position.
Figure 8:
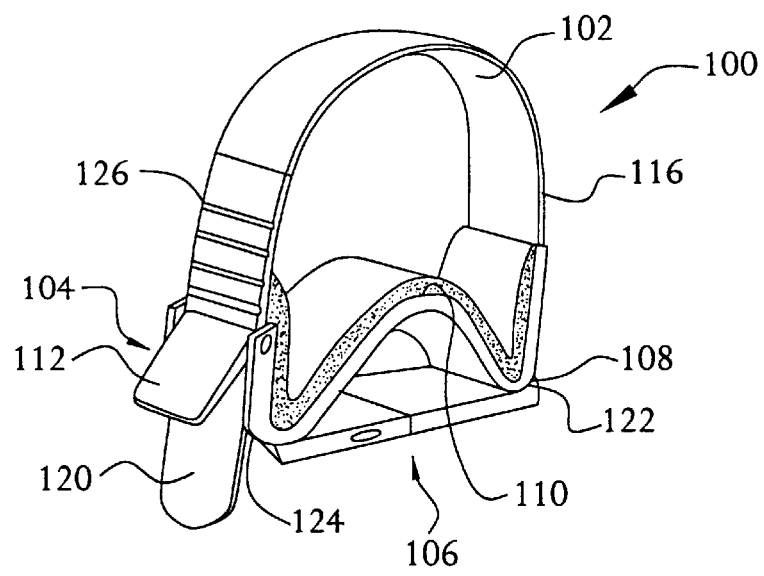
FIG. 8 shows the urethra compression device of FIG. 7 with both the first and second latching mechanisms in a closed position.

FIGS. 7 and 8 illustrate another preferred embodiment of a urethral compression device 100. The compression device 100 has a strap 102, a first latching mechanism 104, a second latching mechanism 106, a hinge set 108, and a compression hinge 110.

The first or closure latching mechanism 104 has a cam lever 112 connected to a receptacle 114 which receives the strap 102. The cam lever 112 is pivotally attached to the receptacle 114. To secure the urethral compression device around the user's penis without applying any undue pressure to specifically cause the urethra to be flattened, the strap 102 is threaded through the receptacle 114 and secured by engaging the cam lever 112 against the strap 102.

In a preferred embodiment, the strap 102 is made from a fabric material 116 and a molded material 118. The strap 102 has a free end 120 which is used with the first or closure latching mechanism 104. The free end 120 is a molded material 118 in the embodiment. It is recognized that the free end 120 could be of a fabric material. The strap 102 is fabric material portion 116 from the free end 120 to a point in proximity to a hinge point 122.

The molded material 118 extends from the receptacle 114 of the first latching mechanism 104 to a point beyond the hinge point 122 of the hinge set 108. The molded material 118 portion of the strap 102 includes both hinge points 122 and 124 of the hinge set 108, the compression hinge 110 and the portions of the second latching mechanism 106 incorporated in the strap 102 as explained below.

The free end 120 of the strap 102 can have a plurality of size indicator markings 126. From these markings 126, a user can locate the predetermined or premeasured point at which the device 100 will be adequately secured to his penis and prevent over or under tightening of the device 100, as seen in FIG. 8 and explained more below with respect to FIGS. 9–11.

The second or compression latching mechanism 106 has a rigid sliding portion 128 which slides into a receptacle portion 130. The second latching mechanism 106 works in conjunction with the hinge set 108 and the compression hinge 110 to secure the compression hinge 110 against a user's urethra. The compression hinge 110 joins a pair of flat pressure-applying elements, which are referred to together as a pressure-applying platform The second latching mechanism 106 can be disengaged by depressing a latch release mechanism 134 and removing the sliding portion 128 from the receptacle portion 130.

Figure 9:
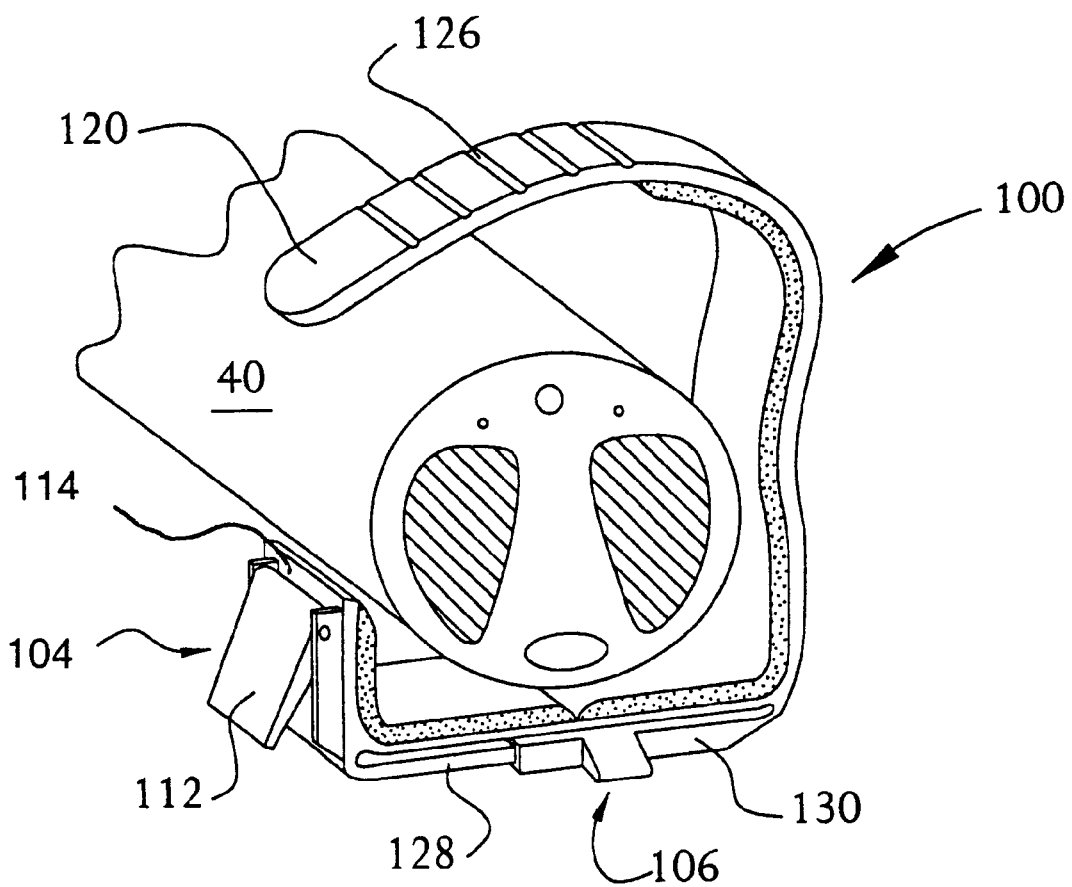
FIG. 9 is a side view of the urethral compression device of FIGS. 7 and 8 with a sectional view of the penile shaft. Both the first and second latching mechanism are in the open position.

In typical operation, both the latching mechanism 104 and 106 of the urethral compression device 100 are in the open position. The user places the urethral compression device 100 around the penis as seen in FIG. 9. The penis is generally in a flaccid state. The user typically slides the urethral compression device 100 over the penis 40, however, the arms can be sufficiently separate such that the penis can pass between the arms.

With both latching mechanisms 104 and 106 of the urethral compression device 100 in an open or unengaged position and the urethral compression device 100 generally around the penis 40, the user positions the device 100 such that the compression hinge 110 which forms the pressure-applying element is located under the urethra 42.

Figure 10:
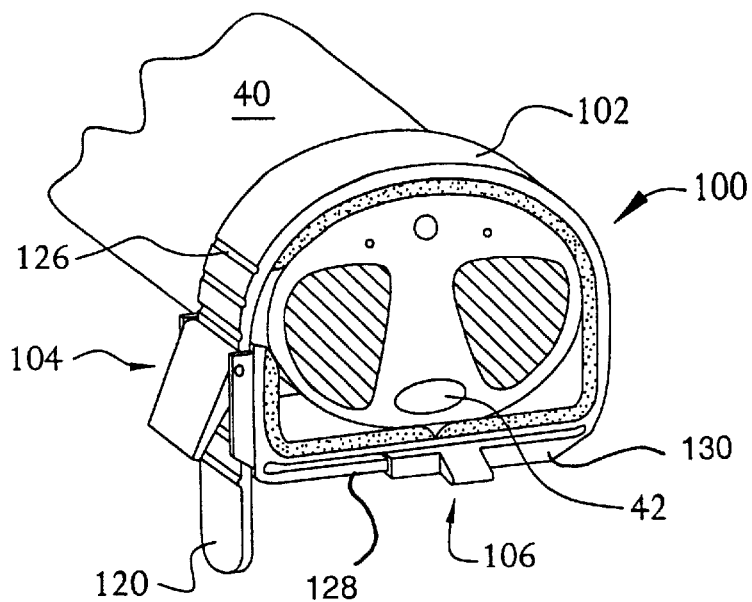
FIG. 10 is a view similar to FIG. 9 with the first latching mechanism closed and the second latching mechanism open.

The user then latches the first or closure latching mechanism 104 so that urethral compression device 100 encircles the penis as seen in FIG. 10. The free end 120 of the strap 102 is slipped through the receptacle 114. The user can either move the strap until the desired size indicator marking 126 is positioned relative to the cam lever 112, or by pulling the strap 102 until proper tauntness is achieved.

It is recognized that for ease, the strap 102 could be of such a length that the free end 120 of the strap is always threaded through the receptacle 114. In this state, the urethra 42 is not compressed or is compressed slightly as seen in FIG. 10.

Figure 11:
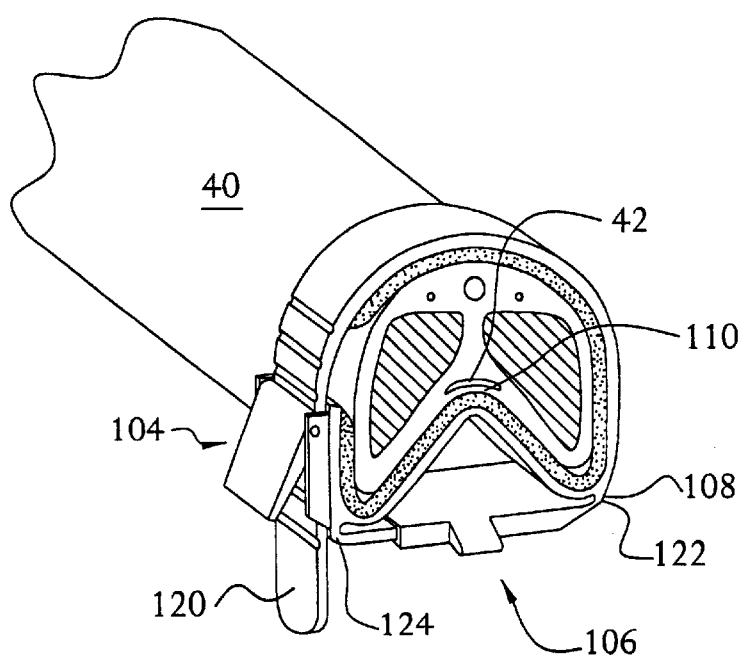
FIG. 11 is a view similar to FIGS. 9 and 10 with both latching mechanisms closed.

To compress the urethra 42, the user moves the second or compression latching mechanism 106 to a closed position as seen in FIG. 11. As the compression latching mechanism 106 moves from an open position to a closed latched position, the hinge set 108 flexes and the compression hinge 110 moves up and exerts pressure on the urethra. The compression hinge 110, which acts as a pressure applying device similar to the previous embodiments, is sized such that when engaging the urethra, the compression hinge has a width that compresses the user's urethra 42 while preventing the user from feeling pinched by unnecessary compression of the penile shaft 40. When the device is in a closed position, the compressing hinge 110, which acts as the pressure-applying element, provides a predetermined degree of depression of the urethra necessary for preventing involuntary urinary flow.

The moving from the position shown in FIG. 10 to that shown in FIG. 11 can alternatively be described as moving the hinge points of the hinge set 108 towards each other. The second ends, the end at the hinge point 122 and 124, of the flat pressure-applying elements are moved towards each other. Typically by pressing the strap in proximity to the hinge points towards each other. The movement of the pressure-applying elements towards each other results in moving the compression hinge 110 towards and into engagement with the penis 40 to compress the urethra 42. The compression latch 106 moves to a closed position to retain the compression hinge 110 which acts as a pressure-applying element in engagement with the penis compressing the urethra. In a preferred embodiment, the compression latching mechanism makes an audible click which allows the user to determine the position of the compression hinge 110.

When the user desires to relieve pressure and open the urethra, the user opens the second or compression latching mechanism 106, using the release mechanism 134 therein returning to what is shown in FIG. 10. In contrast to the previous embodiments, the urethral compression device 100 still totally encircles the penis.

To remove the urethral compression device 100 from a penis, a user can rotate the cam lever 112 thereby allowing strap 102 to loosen.

Figure 12:
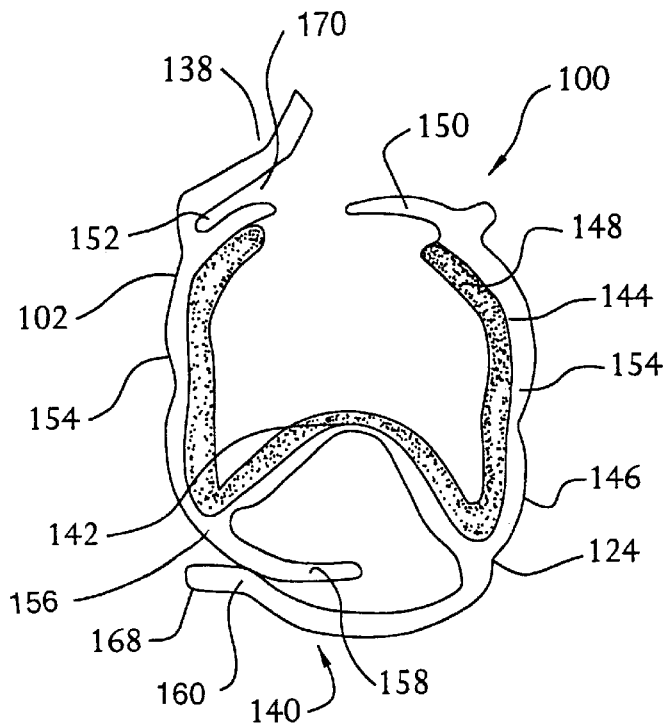
FIG. 12 illustrates an alternative embodiment of the urethral compression device having a first latching mechanism for closing the device and a second latching mechanism for compressing of the urethra.
Figure 13:
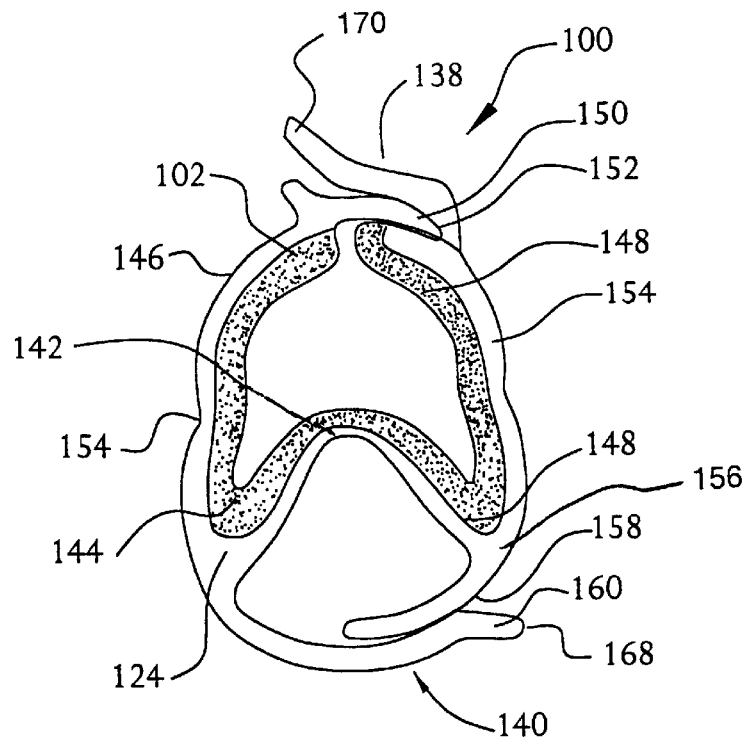
FIG. 13 shows the urethral compression device of FIG. 12 with both latching mechanisms in the closed position.

FIGS. 12 and 13 illustrate another embodiment of the urethral compression device 100. A strap 102 forms the body of the compression device 100. The compression device 100 in addition has a first or closure latching mechanism 138, a second or compression latching mechanism 140 and a compression binge 142.

The strap 102, has both an inner surface 144 and an outer surface 146. In a preferred embodiment, the inner surface 144 of the strap 102 has a padding material 148. The padding material 148 is a foam material or a sponge material. The padding material 148 can provide the user with a degree of comfort when wearing the compression device 100. For example, the padding material 148 can absorb moisture and gives the user the impression that it will prevent pinching of the user's penis by the strap 102 or digging of the edge of the strap into the penis.

In this embodiment, the first latching mechanism 138 has a tooth portion 150 and a tooth receptacle 152. The tooth receptacle 152 forms a channel for receiving the tooth portion 150. The user places the tooth portion 150 into the tooth receptacle 152 such that the device 100 encircles the penis. In a preferred embodiment, either the tooth portion 150 has a plurality of teeth or the tooth receptacle 152 has a plurality of grooves for receiving the teeth to allow for adjustability.

The compression device 100 has a first hinge set 154 and a second hinge set 156. These hinge sets 154 and 156 each have a pair of hinges on the strap 102. The first hinge set 154 is a living hinge both with a reduction in material and a contour shaped which allows the urethral compression device 100 to closely conform to the shape of a user's penis and allow for a secure fit of the compression device 100 around a user's penis. The second hinge set 156 works in conjunction with the compression hinge 142 to assert pressure against the user's urethra.

When engaged, the compression hinge 142 forms the pressure-applying element to compress a user's urethra, thereby preventing fluid flow and alleviating a symptom of incontinence. Similar to the hinge sets 154 and 156, the hinge 142 is formed of a flexible living hinge material of the strap 102.

The second latching mechanism 140 comprises a tooth portion 158 and a tooth receptacle 160. The second latching mechanism 140, when engaged, can adjust the angle in the compression hinge 142 and move the hinge points of the second hinge set 156 closer together. A user can engage and index the tooth portion 158 and the second tooth receptacle 160 to adjust the amount of flexion in the compression hinge 142. As a user moves the tooth portion 158 and second tooth receptacle 160 of the second latching mechanism 140 together, the compression hinge 142 moves towards and impinge the user's urethra.

The first 138 and second 140 latching mechanisms each have a release mechanism 164 and 166 respectively. The release mechanisms 164 and 168 allow a user to release the urethral compression device 100 to allow fluids to pass through the urethra or to allow cleaning of the device or the penis. The release mechanisms 164 and 166 are formed as part of the tooth receptacle 152 and 160 respectively. The tooth receptacles 152 and 160 are biased to a closed engaging position and each have spring tab 168 and 170 to move the tooth receptacle 152 and 160 to their respective open positions.

In typical operation, both the latching mechanism 138 and 140 are in the open position as seen in FIG. 8. The user places the urethral compression device 100 around the penis. The user typically slides the urethral compression device 100 over the penis 40, however, the arms can be sufficiently separate such that the penis can pass between the arms.

With both latching mechanisms 138 and 140 of the urethral compression device 100 in an open position and the urethral compression device 100 generally around the penis 40, the user positions the device 100 such that the compression hinge 142 which forms the pressure-applying element is located under the urethra 42.

The user then latches the first or closure latching mechanism 138 so that urethral compression device 100 encircles the penis. In this state, the urethra 42 is not compressed or is compressed slightly. To compress the urethra 42, the user moves the second or compression latching mechanism 140 to a closed position. As the compression latching mechanism 140 moves from an open position to a closed latched position seen in FIG. 13, the second hinge set 156 flexes and the compression hinge 142 moves up and exerts pressure on the urethra. The compression hinge 142 acts as a pressure applying device similar to the previous embodiments. The device 100 is sized such that when the compression hinge 142 pushes against the urethra, the compression hinge has a width that compresses the user's urethra 42 while preventing the user from feeling pinched by unnecessary compression of the penile shaft 40.

When the user desires to relieve pressure and open the urethra, the user opens the second or compression latching mechanism 140, using the second release mechanism 166. In contrast to the previous embodiments, the urethral compression device 100 still totally encircles the penis.

To remove the urethral compression device 100 from a penis, a user can engage the first release mechanism 164 thereby detaching the first latching mechanism 138 and allowing for the open strap 102 to be removed.

Figure 14:
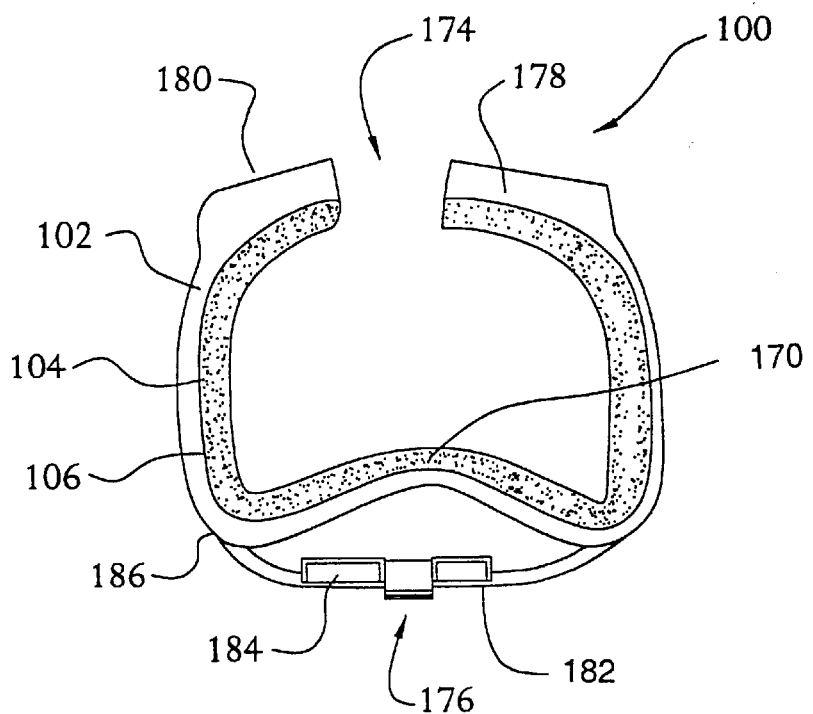
FIG. 14 shows another alternate embodiment of the urethral compression device with both the first and second latching mechanisms in an engaged position.
Figure 15:
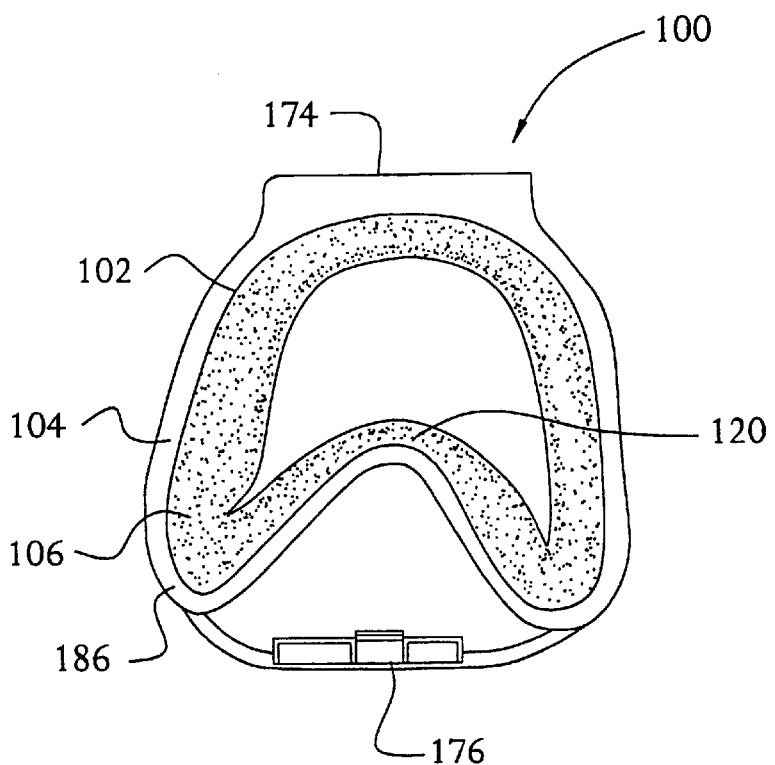
FIG. 15 shows the urethral compression device of FIG. 14 with both the first and second latching mechanisms in an unengaged state.

An alternate embodiment of the urethral compression device 100 is illustrated in FIGS. 14 and 15. The compression device 100 has a first or closure latching mechanism 174 and a second or compression latching mechanism 176.

The first latching mechanism 174 has a sliding portion 178 and a receptacle portion 180. The sliding portion 178 of the first latching mechanism 174 slides into the receptacle portion 180 and locks, as seen in FIG. 15, therein to secure the urethral compression device 100 around the user's penis. In a preferred embodiment, the sliding portion 178 has compressible arms that flex inward as the arms enter the receptacle portion 180 and flex outward in the large area to secure the latching mechanism 174. The first or closure latching mechanism 174 can be disengaged by depressing a latch release mechanism and removing the sliding portion 178 from the receptacle portion 180 to return to an open position shown in FIG. 14.

The second or compression latching mechanism 176 has a sliding portion 182 which slides into a receptacle portion 184. The second latching mechanism 176 can be disengaged by depressing a latch release mechanism and removing the sliding portion 182 from the receptacle portion 184.

The urethral compression device 100 has a single hinge set 186 within the strap 102. The hinge set 186 with its hinge points 188 work in conjunction with the compression latching mechanism 176 to secure a compression hinge 120 against a user's urethra.

The second latching mechanism 176 is shown in a released or disconnected position in FIG. 14 wherein the compression hinge 120 from an engaged state and is shown engaged in FIG. 15, which forces the compression hinge 120 against a user's urethra.

In addition to the hinge set 186, the strap 102 can flex as a non-localized hinge to allow opening and closure. The hinge set 186 of the urethral compression device flexure to allow opening and closure of both latching mechanisms 174 and 176.

Figure 16:
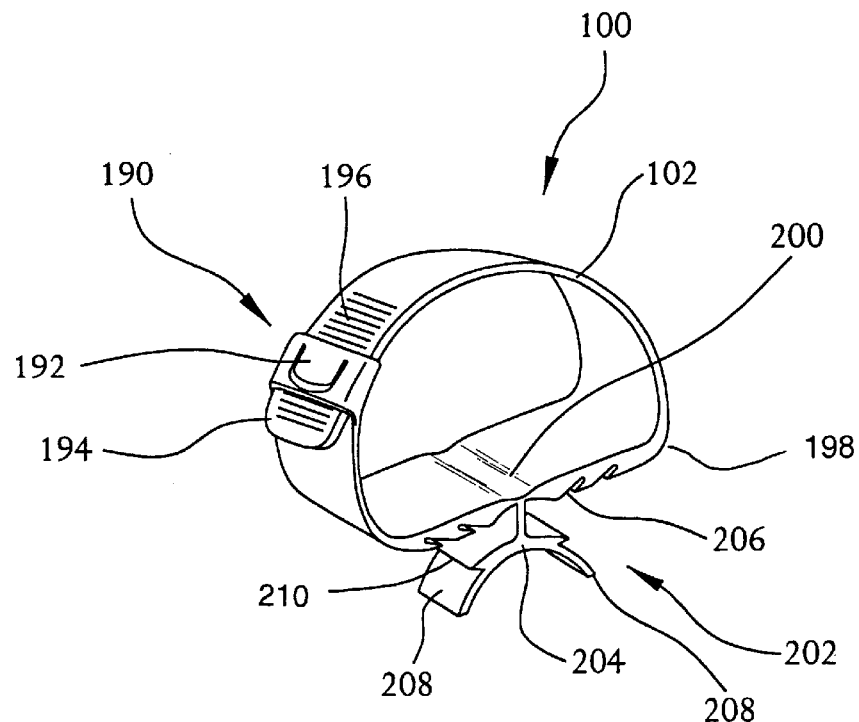
FIG. 16 illustrates an alternate embodiment of a urethral compression device.
Figure 17:
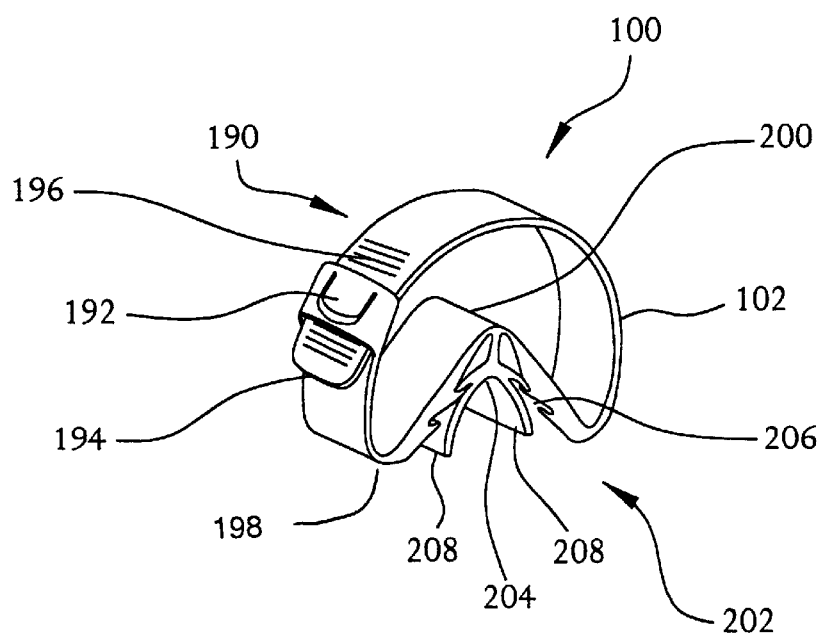
FIG. 17 illustrates the urethral compression device of FIG. 16 with both the first and second latching mechanisms in an engaged state. The first latching mechanism has a slide tightener which is shown exploded out.

Another alternate embodiment of the urethral compression device 100 is illustrated in FIGS. 16 and 17. The strap 102 forms the body of the compression device 100. The compression device 100 has a first or closure latching mechanism 190. The first latching mechanism 190 which is referred to as a zip tie latching mechanism, has a zip tie latch 192 with a detent mechanism and a zip tie strap 194 with a plurality of closely spaced grooves 196. To secure the urethral compression device on a user's penis, the zip tie strap 194 is threaded through the zip tie latch 192. The detent of the zip tie latch engages one of the grooves 196 of the zip tie line 194 as a user indexes the zip tie line 194 through the latch 192, thereby securing the urethral compression device 100 around the user's penis. The user releases the urethral compression device 100 from his penis by lifting the zip tie latch 192, thereby spacing the detent from the grooves 196 on the zip tie line 194 and allowing the zip tie line 194 to be loosened by the user.

The urethral compression device 100 has a pair of hinge points 198 which define a hinge set. The strap 102 is flexible and conforms the penis from one of the hinge points 198 to the other hinge points for the portion that does not include the compression hinge 200.

The urethral compression device 100 has a second latching mechanism 202 with a wishbone latch 204 and a latch receptacle 206, which is formed on the outer surface of the strap 102 between the compression hinge 200 and each of the hinge points 198. The wishbone latch 204 has a pair of wishbone ends 208, each with engaging tabs 210. The motion of the wishbone latch 204 engaging the latch receptacle 206 forces the compression hinge 200 toward the urethra of the user. The compression of the strap 102 of the urethral compression device 100 near the hinge points 198 moves the compression hinge 200 upward. The engaging tabs 210 of wishbone latch 204 pass over and engage the latch receptacle 206 to retain the compression hinge 200 which acts as the pressure-applying element can be secured into place against the user's urethra. Similar to previous embodiments, the compression hinge, which acts as a pressure applying device, is sized such that when engaging the urethra, the compression hinge has a width that compresses the user's urethra but does not unnecessarily compress the remainder of the penile shaft.

To release the compression hinge 200, the wishbone ends 208 are compressed together, thereby releasing the wishbone latch 204 from the latch receptacle 206. The compression hinge 200 is then free to move away from the user's urethra.

The first latching mechanism 190 is shown in FIG. 16 with the zip tie strap 194 inserted in the zip tie latch 192, but in a looser state which allows the device to be removed from around the user's penis. The second latching mechanism 202 is unengaged which allows the release of the compression hinge 200 from an engaged state against a urethra. FIG. 17 illustrates the urethra compression device 100 in an engaged state. The first latching mechanism 190 is secured in this embodiment, thereby forcing the strap 102 to enclose a penis. The second latching mechanism 202 is similarly engaged in this embodiment, which forces the compression hinge 200 against a user's urethra.

Figure 18:
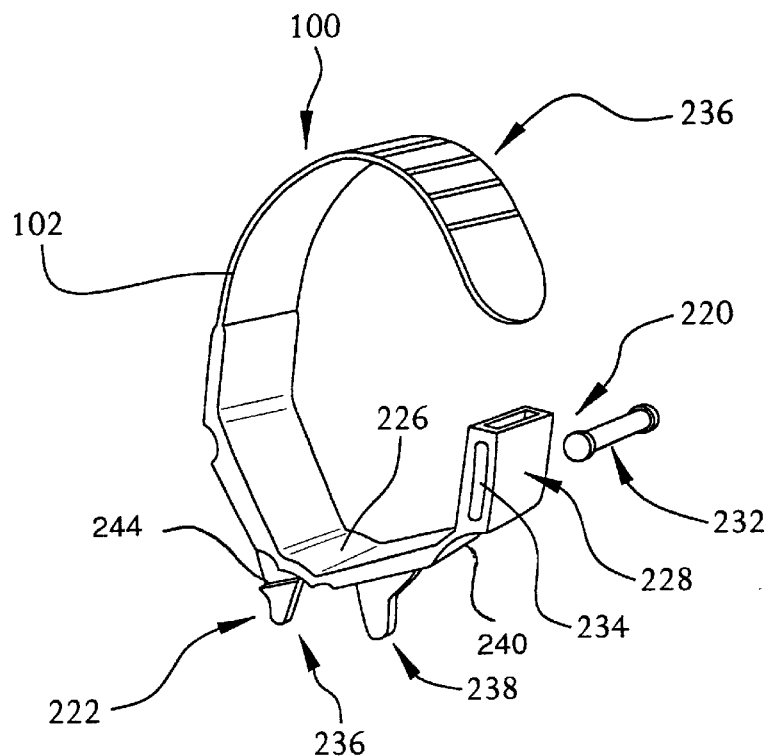
FIG. 18 shows an alternate embodiment of a urethral compression device with the first and second latching mechanisms in an unengaged state.
Figure 19:
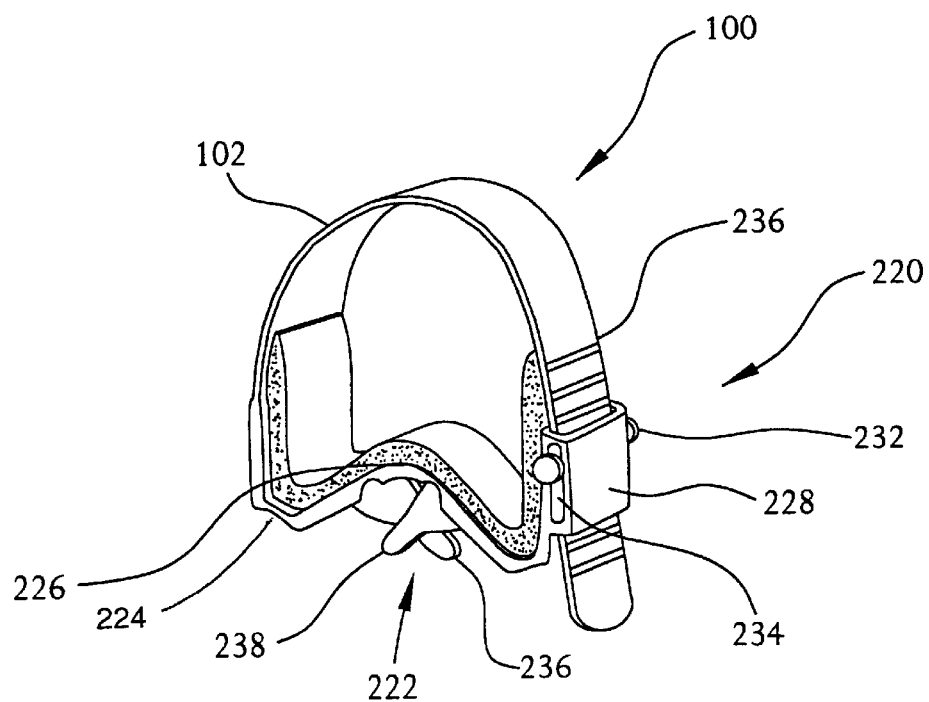
FIG. 19 shows the urethral compression device in FIG. 18 with the first and second latching mechanisms in an engaged state.

Another alternate embodiment of the urethral compression device 100 with a different style latching mechanism is illustrated in FIGS. 18 and 19. The compression device 100 has a strap 102, a first latching mechanism 220, a second latching mechanism 222, a hinge set 224, and a compression hinge 226. The first or closure latching mechanism 180 has a receptacle 228 which receives the free end of the strap 102. The receptacle 228 has a slide tightener 232 which travels within a slot 234. To secure the urethral compression device around the user's penis, the strap 102 is threaded through the receptacle 228 and the proper length positioned. The slide tightener 232 moves within the slot 234 from a released, raised position to an engaged, lowered position as seen in FIG. 19. The slide tightener 232 is moved to the engaged, lowered position. The tension of the strap 102 attempting to pull out keeps the slide tightener 232 in position.

The strap 102 in a preferred embodiment has a plurality of size indicator markings 236 on the surface of the strap 102. From these markings 236, a user can locate the predetermined or premeasured point at which the device 100 will be adequately secured around his penis and prevent over or under tightening of the device 100. A user releases the urethral compression device 100 from his penis by moving the slide tightener 232 from the engaged, lowered position to the released, raised position within the slot 234, thereby allowing the strap 102 to be removed from the receptacle 228 and the compression device 100 to slip off the user's penis.

The second or compression latching mechanism 222 which works in conjunction with the compression hinge 226 to compress the urethra. The second latching mechanism 222, referred to in this embodiment as a one position ratchet, has a first ratchet arm 236 and a second ratchet arm 238. To compress a urethra, the user moves the first and second ratchet arms 236 and 238 toward each other by moving the strap 102 in proximity to the hinge points 240 of the hinge set 224 towards each other or engages the fingers 242 of the ratchet arms 236 and 238 and moving them towards the opposite hinge point 240. This motion of the ratchet arms 236 and 238 forces the compression hinge 260 toward the urethra of the user. The ratchet arms 236 and 238 each have a locking ramp 244 which slide past each other and engage as seen in FIG. 14, the compression hinge 226 is secured to form the pressure applying device to compress the user's urethra.

To release the compression hinge 226 from a locked or secured position, the first and second ratchet arms 236 and 238 are separated to cause the locking ramps 244 to disengage, thereby providing for removal of the compression hinge 226 from the user's urethra.

Figure 20:
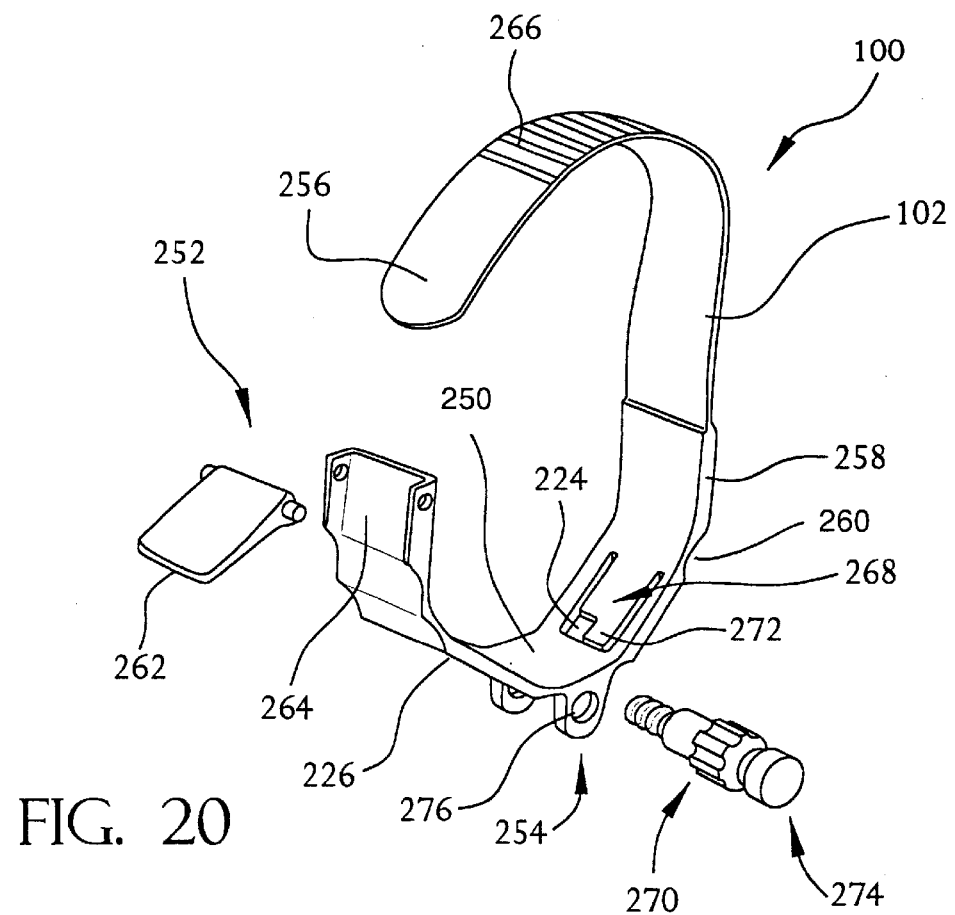
FIG. 20 illustrates another alternate embodiment of a urethral compression device with the first and second latching mechanisms in an unengaged state. The cam lever of the first latching mechanism and the ratchet of the second latching mechanism are shown.
Figure 21:
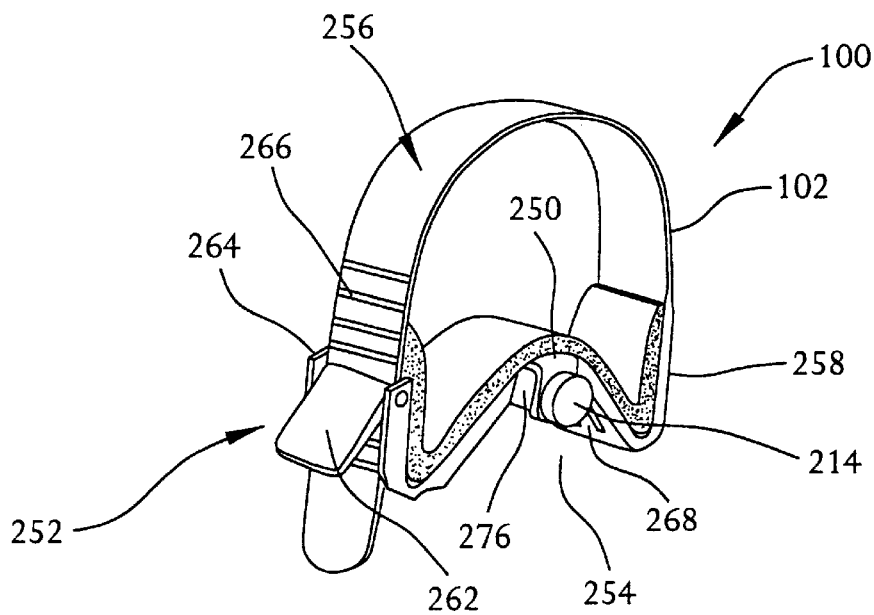
FIG. 21 illustrates the urethral compression device in FIG. 20 with the first and second latching mechanisms in an engaged state.

Another alternate embodiment of the urethral compression device 100 is illustrated in FIGS. 20 and 21. The compression device 100 has a strap 102, a hinge set 248, a compression hinge 250, a first or closure latching mechanism 252 and a second or compression latching mechanism 254.

In a preferred embodiment, the strap 102 is made from a fabric material 256 and a molded material 258 which can be molded over a portion of the fabric 256. The molded material 256 extends from the first latching mechanism 252 to a point beyond a hinge point 260 of the hinge set 248. The molded material 258 portion of the strap 102 includes both hinge points 260 of the hinge set 248, the compression hinge 250 and the portions of the second latching mechanism 254 incorporated in the strap 102 as explained below.

The first latching mechanism 252 has a cam lever 262 connected to a receptacle 264 which receives the strap 102. The cam lever 262 is pivotally attached to the receptacle 264. To secure the urethral compression device 100 around the user's penis, the strap 102 is threaded through the receptacle 264 and secured by engaging the cam lever 262 against the strap 102.

The strap 102 can have a plurality of size indicator markings 266 on the surface of the strap. From these markings 266, a user can locate the predetermined or premeasured point at which the device 100 will be adequately secured to his penis and prevent over or under tightening of the device 100. A user can release the urethral compression device 100 from his penis by releasing the cam lever 262 from a locked position over the receptacle 264, thereby allowing the strap 102 to be loosened and the device 100 removed from the user's penis.

The second latching mechanism 254 which is located near the compression hinge 250, has a notched pawl 268 formed integrally with the molded material 258 portion of the strap 102, and a ratchet 270. The notched pawl 268 has a pawl portion 272 and is surrounded by a notch or void portion of the strap 102. The ratchet is mounted to a pin 274 which is housed in a pin receptacle 276 on the urethral compression device 100 at the compression hinge 250.

To compress a urethra, the user aligns the ratchet 270 with the pawl portion 272 of the notched pawl 268. The user then raise the pin receptacle 276 towards his urethra by pushing the strap 102 in proximity to the hinge points 260 towards each other. This raising motion forces the compression hinge 250 against the user's urethra.

The pawl portion 272 of the notched pawl 268 engages the ratchet 270 mounted on the pin 274. When the ratchet 270 is engaged by the pawl portion 272, the compression hinge 250 will remain engaged against the user's urethra until released.

To release the compression hinge 250, the user depresses the pin 274 so that the ratchet 270 aligns with the void portion of the notched pawl 268. With the pawl portion 272 of the notched pawl 268 no longer engaging the ratchet 270, the compression hinge 250 can be released from the user's urethra.

FIGS. 22 and 23 illustrate an alternate embodiment of the urethral compression device 100. Similar to the previous embodiment, the urethral compression device 100 has a strap 102, a hinge set 278, a compression hinge 280, a first latching mechanism 282 and a second latching mechanism 284. Likewise, the straps 102 are made from a fabric material 286 and a molded material 288. The molded material 288 in this embodiment extends from a portion of the first latching mechanism to just before the hinge point. The molded material 288 portion of strap 102 includes the compression hinge 280, the second latching mechanism 284 and portions of the first latching mechanism 282 as explained below. In contrast to the previous embodiment, the hinge points 290 of the hinge set 278 are living hinges formed from the fabric material 286 portion of the strap 102 in proximity to the molded material 288.

The first latching mechanism 282 has a first and a second buckle portion slots 292 and 294. The slots 292 and 294 are located on the molded material 288 portion of the strap 102 and on opposite sides of the compression hinge 280. The first latching mechanism has a tooth 296 projecting into one of the slots 292 and 294. To secure the compression device 100 to a penis, a user threads the free end of the strap 102 through the first buckle portion 292 and the second buckle portion slot 294 along the strap thread path 298. In a preferred embodiment, the strap 102 has a plurality of apertures 300 located near the free end. The strap 102 is pulled to the proper position wherein one of the apertures fits around the tooth 296 projecting into the second buckle portion slot 294, such as seen in FIG. 23, to secure the device 100 around his penis. A user can release the urethral compression device 100 from his penis by releasing the strap 102 from the tooth 296, thereby allowing the strap 102 to be loosened, as seen in FIG. 22, and the device 100 removed from the user's penis.

The second or compression latching mechanism 284 has a pair of ratchets 302 and a pair of pawls 304. In a preferred embodiment, the ratchets 302 are each one position ratchets or detaching grooves, each for receiving and holding a pawl 304 when the second latching mechanism 284 is in an engaged or closed position. When a user tightens the strap 102 within the first latching mechanism 282, this motion can cause the compression hinge 120 to flex and move toward the user's urethra.

To compress the urethra, the user moves the strip 102 in proximity to the hinge points 290 of the hinge set 278 towards each other which results in the compression hinge 280 with a pair of flexible portions 306 moving towards the user's urethra. The pawls 304 engage the ratchets 302 of the second latching mechanism 284 to retain the compression hinge 280 against his urethra. To release the compression hinge 280 the user can depress the pawl 304, releasing the ratchet 302, allowing the compression hinge 280 to be moved away from the user's urethra.

An alternate embodiment of the urethral compression device 320 is shown in FIGS. 24 and 25. In contrast to the previous several embodiments, the urethral compression device 320 has only one latching mechanism 322 to both close the opening to retain the urethral compression device 320 around a user's penis and engage the compression mechanism against a user's urethra. In contrast to the first embodiment, the pressure applying device is created by a compression hinge 324. The latching mechanism 322 having a zip tie latch 326 and a zip tie line 328. The zip tie line 328 has a plurality of grooves or openings which are used to secure the zip tie line 328 within the zip tie latch 326 which has a tooth. To secure the compression device 320 to a penis and impinge a urethra, a user can thread the zip tie line 328 through the zip tie latch 326. Pulling the line 328 though the latch 326 can secure the urethral compression device 320 around the user's penis. The pulling of the line 328 will also cause the compression hinge 324 to move toward the urethra, thereby compressing it. The teeth of the zip tie line 328 secures the line 328 within the latch 326.

FIGS. 26 and 27 show an alternate embodiment of a urethral compression device 320 having one latching mechanism 336 to secure the compression device to a user's penis and to engage the compression hinge 338, which acts as a pressure applying device against a user's urethra. The latching mechanism 336 has a pair of latches 340. The latches 340 are located at the hinge points 342 and each have a ratchet 344 and a pawl 346. The pawl 346 can be hingedly connected to the strap. To secure the compression device 320 to a penis and impinge a urethra, a user can push a compression hinge 338 toward his urethra. As the hinge moves toward the urethra, the ratchet 344 will engage the pawl 346, thereby securing the device 320 to a user's penis. Further motion of the compression hinge 338 can impinge a user's urethra. The latching mechanism 336 can further comprise a release button 348. To release the device, a user can depress the release button 348 which will force the pawl 346 from the ratchet 344 and allow the compression hinge 338 to be pulled away from the user's urethra.

FIGS. 28 and 29 illustrate an alternate to the above embodiment of the invention. In this alternate embodiment, the strap 102 further comprises a strap latch 354. The strap latch 354 does not secure the device 320 to the penis. The purpose of the strap latch 354 is to provide for quick and easy application and removal of the compression device 320. The strap latch 354 can have a male portion 356 and a female portion 358. The male portion 356 can attach to the female portion 358 to form a secure connection of one half of the strap to the other.

FIGS. 30 and 31 illustrate another preferred embodiment of a urethral compression device 360. The compression device 360 has a strap 362, a first latching mechanism 364, a second latching mechanism 366, a hinge set 368, and a compression hinge 370.

The first or closure latching mechanism 364 has a locking tab 372 which projects inwardly into a receptacle 374 which receives the strap 362. The receptacle 374 with the locking tab 372 is sometimes referred to as a strap catching element. To secure the urethral compression device around the user's penis without applying any undue pressure to specifically cause the urethra to be flattened, the strap 362 is threaded through the receptacle 374 and secured by engaging the locking tab 372 against the strap 362. To release the strap 362, the locking tab 372 is depressed to disengage from the strap 362.

In a preferred embodiment, the strap 362 is made from a fabric material 376. The strap 362 has a free end 380 which is used with the first or closure latching mechanism 364. The free end 380 of the strap 362 is sometimes referred to as a flexible joining strap.

The molded material 378 extends from the receptacle 374 of the first latching mechanism 364 to a point beyond a hinge point 382 of the hinge set 368. The molded material 378 portion of the strap 362 includes both hinge points 382 and 384 of the hinge set 368, and the compression hinge 370.

The free end 380 of the strap 362 can have a plurality of size indicator markings 386. In contrast to several embodiments described above, the marking 386 are just lines and do not effect how the locking tab 372 engages the strap 362. From these markings 386, a user can locate the predetermined or premeasured point at which the device 360 will be adequately secured to his penis at which the device 360 will be adequately secured to his penis and prevent over or under tightening of the device 360.

In that the strap catching element of the closure latching mechanism engages the free end of the flexible joining strap at infinite positions, it allows the device to be fitted to any penile circumference within the range of the strap size provided. Furthermore, the infinite adjustability afforded by the strap allows the user to bring the closure latching or strap mechanism to the same degree of fit each time, allowing for changes in penile circumference which can result from physical exertion or environment conditions.

The second or compression latching mechanism 366 which works in conjunction with the compression hinge 370 to compress the urethra. The compression hinge 370 joins a pair of flat pressure-applying elements, which are referred together as a pressure-applying platform The second latching mechanism 366, referred to in this embodiment as a multi-position ratchet, has a ratchet arm or rack 388 having a plurality of teeth 390 which define receptacles 392, and an engaging tab or tooth 394. To compress a urethra, the user moves the strap 362 in proximity to the hinge points 382 and 384 of the hinge set 368 towards each other. The compression of the strap 102 of the urethra compression device 100 near the hinge points 198 moves the compression hinge 205 upward. The engaging tab 394 passes over and engages the latch receptacle 392 to retain the compression hinge 370 which acts as the pressure-applying element can be secured into place against the user's urethra. Similar to previous embodiments, the compression hinge, which acts as a pressure applying device, is sized such that when engaging the urethra, the compression hinge has a width that compresses the user's urethra but does not unnecessarily compress the remainder of the penile shaft.

In describing the movement from the position of the closure latching mechanism latched and the compression latching mechanism open to both latching mechanisms in the closed engaged position, the hinge points of the hinge set are moved towards each other. The second ends, the end at the hinge point, of the flat pressure-applying elements are moved towards each other. Typically by pressing the strap in proximity to the hinge points towards each other. The movement of the pressure-applying elements towards each other results in moving the compression hinge perpendicular to the motion of the second ends of the pressure-applying element end towards and into engagement with the penis to compress the urethra The compression latch moves to a closed position to retain the compression hinge which acts as a pressure-applying element in engagement with the penis compressing the urethra. In a preferred embodiment, the compression latching mechanism makes an audible click which allows the user to determine the position of the compression hinge 370.

The compression hinge 205 forms the apex of a triangle with the distance between the second ends of the flat pressure-applying elements or hinge points forming the base.

To release the compression hinge 370, a releasing tab 398 of the engaging tab 394 is flexed away from the ratchet arm 388, thereby releasing the engaging tab 394 from the latch receptacle 392. The compression hinge 370 is then free to move away from the user's urethra.

As seen from the above embodiments, the urethral compression device can have various different forms. The compression device can have a closure latching mechanism and a compression latching mechanism, or a latching mechanism that serves both purposes. The urethral compression device can have a plurality of hinge sets. The hinge sets can be formed of flexible material, such as a living hinge formed from the strap, or two separate portions of strap with a distinct hinge pin. The compression device can have a preformed pressure applying device or one that is formed as a compression hinge moves. However, in all embodiments, the pressure applying devices are sized to compress the urethra while preventing the user from feeling pinched by unnecessary compression of the penile shaft 40.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A urethral compression device comprising:
   a strapping device for enclosing the penis;
   a compression hinge which folds into a position compressing a urethra carried by the strapping device for compressing the urethra and having a width of between 100 percent and 150 percent of the urethra; and
   a latching mechanism for retaining the compression element in a radially inward position to compress the urethra of the penis.

2. A urethral compression device comprising:
   a strapping device for enclosing the penis;
   a generally rigid and cylindrical compression element carried by the strapping device for compressing the urethra and having a width of between 100 percent and 150 percent of the urethra; and
   a latching mechanism for retaining the compression element in a radially inward position to compress the urethra of the penis.

3. The urethral compression device of claim 2 wherein the strapping device is an arc shaped member having a first end and a second end such that the ends move from a closed position to an open position in response to an intrinsic stress member; and the latching mechanism is a connector to connect the first end and the second end such that the arc shaped member is under stress.

4. The urethral compression device of claim 1 wherein the latching mechanism is a compression latching mechanism for retaining the compression hinge in a position to compress the urethra and further comprising a closure latching mechanism for securing the strapping device.

5. The urethral compression device of claim 1 wherein the strapping device is contiguous for encircling the penis and the latching mechanism moves the compression hinge toward the urethra for both securing the strapping device and compressing the urethra.

6. A urethral compression device comprising:
   a strapping device adapted for enclosing a penis, the strapping device having a first arm having a flexible joining strap, a second arm with a strap catching element for receiving the flexible joining strap, and a pressure-applying platform;
   a pressure adjustment devices for adjusting the pressing force exerted by the pressure-applying platform to the underside of the penis, the pressure adjustment device having a latching mechanism for retaining the pressure-applying platform in a position exerting pressure against the urethra.

7. The urethral compression device of claim 6 wherein the pressure-applying platform comprises a pair of substantially-flat pressure-applying elements which are hingedly connected to each other and each pressure-applying element connected to one of the arms of the strapping device.

8. The urethral compression device of claim 7, wherein the latching mechanism has a pair of latching surfaces for engaging each other for retaining the latching mechanism in a latched position and each of the pressure-applying elements carrying one of the latching surfaces.

9. The urethral compression device of claim 7, wherein the latching mechanism has a tooth carried by one of the pressure-applying elements and the rack defining a plurality of notches for retaining the tooth in a latched position, the rack carried by the other pressure-applying element.

10. The urethral compression device of claim 9 wherein the one of the pressure-applying elements with the tooth has a release tab and the rack defining the notches is curved.

11. The urethral compression device of claim 9 wherein the flexible joining strap of the first arm of the strapping mechanism is a webbing material of nature or synthetic fibers which is joined connected to said first arm by a suitable chemical or mechanical bonding means.

12. The urethral compression device of claim 10 wherein the degree of compression is provided by a preset increments of the latching mechanism and audible and tactile indication generated by the feedback of the latching mechanism assures the user to quickly reach the degree of compression necessary for his personal need.

13. The urethral compression device of claim 10 wherein the strap catching element has a receptacle for receiving the flexible joining strap and a locking tab projecting into the receptacle for engaging the strap.

14. A urethral compression device for compressing the urethra of a penis, the device comprising:
   a strapping device for enclosing the penis, the strapping device comprising an inner surface, an outer surface and a compression hinge which folds into a radially inward position compressing the urethra;
   a first latching mechanism carried by the strapping device for securing the strapping device to the penis; and
   a second latching mechanism for retaining the compression hinge of the strapping device in the radially inward position to compress the urethra of the penis.

15. The compression device of claim 14 wherein the strapping device comprises a plurality of hinge joints.

16. The compression device of claim 15 wherein the strapping device comprises at least three hinge joints.

17. The compression device of claim 14 wherein the inner surface of the device comprises a padding material.

18. The compression device of claim 17 wherein the padding material comprises a foam material.

19. The compression device of claim 18 wherein the padding material is sponge material.

20. The compression device of claim 14 wherein the first latching mechanism comprises a tooth portion and a tooth receptacle.

21. The compression device of claim 14 wherein the first latching mechanism comprises a sliding portion and a receptacle portion.

22. The compression device of claim 21 wherein the sliding portion further comprises at least one compressible arm which, when engaged with the receptacle portion, expands to secure the slidable portion within the receptacle portion.

23. The compression device of claim 14 wherein the second latching mechanism comprises a ratchet.

24. The compression device of claim 23 wherein the ratchet comprises a wishbone latch and a wishbone receptacle.

25. The compression device of claim 23 wherein the ratchet comprises a first ratchet arm and a second ratchet arm.

26. A urethral compression device for compressing the urethra of a penis, the device comprising:

a strapping device for enclosing the penis;

a compression hinge carried by the strapping device and the compression hinge extending transverse across the strapping device and adapted to extend longitudinally along the urethra and folds into a position for compressing the urethra; and a latching mechanism for retaining the compression element in a radially inward position to compress the urethra of the penis.

27. The urethral compression device of claim 26 wherein the latching mechanism is a compression latching mechanism for retaining the compression hinge in a position to compress the urethra and further comprising a closure latching mechanism for securing the strapping device.

28. The urethral compression device of claim 21 wherein the compression hinge is formed by a pair of substantially flat pressure-applying elements and the compression hinge has a width of between 100 percent and 150 percent of the urethra when the compression latching mechanism is in a latched position.

29. The urethral compression device of claim 28 wherein the compression latching mechanism is a multi-position ratchet with a ratchet arm having a plurality of teeth defining receptacles and an engaging tab for engaging the receptacles, the multi-position ratchet carried by one of the flat pressure-applying elements and the engaging tab carried by the other flat pressure-applying elements.

30. A method of compressing a urethra comprising the following steps:

providing a urethral compression device having a pressure-applying element and a compression latching mechanism, the pressure-applying element having a pair of substantially flat pressure-applying elements hinged together at a first end forming a compression hinge, and each of the flat pressure-applying elements having a second end;

encircling the penis with the urethral compression device;

aligning the pressure-applying element with the urethra;

moving the second ends of the flat pressure-applying elements towards each other therein moving the compression hinge towards and into engagement with the penis to compress the urethra; and the movement of the second ends therein resulting in moving the compression latching mechanism into a closed latched position retaining the compression hinge against the penis.

31. The method of compressing a urethra of claim 30 further comprising the steps of:

providing a closure latching mechanism having a strap element and a strap catching element;

inserting the strap element in the strap catching element; and latching the closure latching mechanism without applying any undue pressure to specifically cause the urethra to be flattened.

32. The method of compressing a urethra of claim 31 wherein the step of moving the second ends of the flat pressure-applying results in the compression hinge forming a pressure-applying element having a width of between 100 percent and 150 percent of the urethra.

33. The method of compressing the urethra of claim 32 further comprising the step of clicking the compression latching mechanism to indicate an extent of compression.

34. The method of compressing the urethra of claim 33 further comprising the step of releasing the compression latching mechanism to allow opening the urethra, and still encircling the penis with the urethral compression device.

35. A method of compressing a urethra comprising the following steps:

providing a urethral compression device having a longitudinally extending pressure-applying element, a compression mechanism, and a closure latching mechanism, the pressure-applying element having a pair of substantially flat pressure-applying elements hinged together at a first end forming a compression hinge, and each of the flat pressure-applying elements having a second end;

encircling the penis with the urethral compression device;

aligning the longitudinally extending pressure-applying element with the urethra;

latching the closure latching mechanism without applying any undue pressure to specifically cause the urethra to be flattened;

moving the second ends of the flat pressure-applying elements towards each other therein moving the compression hinge towards and into engagement with the penis to compress the urethra; and the movement of the second ends therein resulting in moving the compression latching mechanism into a closed latched position retaining the compression hinge against the penis.

36. The method of compressing the urethra of claim 35 further comprising the step of releasing the compression latching mechanism to allow opening the urethra, and still encircling the penis with the urethral compression device.

37. The method of compressing the urethra of claim 36 further comprising the step of clicking the mechanism to indicate an extent of compression.

38. A urethral compression device for compressing the urethra of a penis, the urethral compression device comprising:

a strapping device for enclosing the penis;

a compression device carried by the strapping device, the compression device having a pressure-applying element adapted to extend longitudinally along the urethra, the pressure-applying element formed from a compression hinge that folds into a radially inward position compressing the urethra, the compression device having a latching mechanism for retaining the compression element in a radially inward position to compress the urethra of the penis.

39. The urethral compression device of claim 38 wherein the strapping device has a first end and a second end and further comprising a latching mechanism for securing the first end and the second end therein the strapping device encircling the penis.

* * * * *

UNITED STATES PATENT AND TRADEMARK OFFICE
CERTIFICATE OF CORRECTION

PATENT NO. : 6,289,895 B1
DATED : September 18, 2001
INVENTOR(S) : Cheng et al.

It is certified that error appears in the above-identified patent and that said Letters Patent is hereby corrected as shown below:

Column 19,
Line 9, please delete "of claim 18" and insert -- of claim 17 --;
Line 46, please delete "of claim 21" and insert -- of claim 27 --.

Signed and Sealed this

Sixteenth Day of July, 2002

Attest:

Attesting Officer

JAMES E. ROGAN
Director of the United States Patent and Trademark Office